United States Patent
Tarricone et al.

(10) Patent No.: US 9,931,227 B2
(45) Date of Patent: Apr. 3, 2018

(54) INTERVERTEBRAL PROSTHESIS, APPARATUS FOR IMPLANTING INTERVERTEBRAL PROSTHESES AND SURGICAL METHOD FOR IMPLANTING INTERVERTEBRAL PROSTHESES, PARTICULARLY FOR PERCUTANEOUS MINIMALLY-INVASIVE SURGICAL PROCEDURES

(71) Applicant: REDEMED S.R.L., Lucca (IT)

(72) Inventors: Luigi Tarricone, Surbo (IT); Luca Antonelli, Lecce (IT)

(73) Assignee: REDEMED S.R.L., Lucca (IT)

( * ) Notice: Subject to any disclaimer, the term of this patent is extended or adjusted under 35 U.S.C. 154(b) by 32 days.

(21) Appl. No.: 14/657,803

(22) Filed: Mar. 13, 2015

(65) Prior Publication Data

US 2016/0262911 A1  Sep. 15, 2016

(51) Int. Cl.
| | | |
|---|---|---|
| A61F 2/44 | (2006.01) | |
| A61B 17/88 | (2006.01) | |
| A61F 2/46 | (2006.01) | |
| A61B 17/16 | (2006.01) | |

(52) U.S. Cl.
CPC ........ *A61F 2/4611* (2013.01); *A61B 17/1659* (2013.01); *A61B 17/1671* (2013.01); *A61F 2/442* (2013.01); *A61F 2/4455* (2013.01); *A61F 2/4465* (2013.01); *A61F 2/4657* (2013.01); *A61F 2002/4475* (2013.01); *A61F 2002/4627* (2013.01); *A61F 2002/4629* (2013.01); *A61F 2002/4635* (2013.01); *A61F 2002/4661* (2013.01); *A61F 2002/4677* (2013.01)

(58) Field of Classification Search
CPC ...... A61F 2/4611; A61F 2/442; A61F 2/4465; A61F 2/4657; A61F 2002/4475; A61F 2002/4629; A61F 2002/4635; A61F 2002/4661; A61F 2002/4677; A61B 17/1659; A61B 17/1671
USPC ........... 623/17.11, 17.16; 606/246, 279, 104, 606/86 A
See application file for complete search history.

(56) References Cited

U.S. PATENT DOCUMENTS

| | | | |
|---|---|---|---|
| 2004/0230100 A1 | 11/2004 | Shluzas | |
| 2005/0222681 A1* | 10/2005 | Richley | A61F 2/446 623/17.11 |
| 2006/0217806 A1* | 9/2006 | Peterman | A61F 2/4455 623/17.11 |

(Continued)

FOREIGN PATENT DOCUMENTS

WO    2014026017 A1    2/2014

OTHER PUBLICATIONS

Written Opinion and Search Report of International Application No. PCT/EP2016/055346; dated Jun. 10, 2016; 16 pages.

*Primary Examiner* — Pedro Philogene
*Assistant Examiner* — David C Comstock
(74) *Attorney, Agent, or Firm* — Brooks Kushman P.C.

(57) ABSTRACT

An intervertebral prosthesis, particularly for percutaneous minimally-invasive surgery having a substantially disc-like geometry with a thickness equal to the intervertebral distance to be restored is provided. In a lateral elevation view, in the intervertebral prosthesis there is a through-hole adapted to allow its sliding along a guiding wire inserted previously in the patient through a percutaneous minimally-invasive anterolateral access.

35 Claims, 17 Drawing Sheets

(56) References Cited

U.S. PATENT DOCUMENTS

| | | |
|---|---|---|
| 2006/0217807 A1* | 9/2006 | Peterman .............. A61F 2/4455 623/17.11 |
| 2006/0253201 A1 | 11/2006 | McLuen |
| 2007/0156239 A1 | 7/2007 | Lipnick et al. |
| 2010/0168798 A1 | 7/2010 | Clineff et al. |
| 2010/0331883 A1* | 12/2010 | Schmitz ............. A61B 10/0275 606/249 |
| 2012/0035730 A1 | 2/2012 | Spann |
| 2013/0158668 A1 | 6/2013 | Nichols et al. |
| 2014/0067069 A1* | 3/2014 | Lopez ................... A61F 2/4425 623/17.16 |

\* cited by examiner

INTERVERTEBRAL PROSTHESIS, APPARATUS FOR IMPLANTING INTERVERTEBRAL PROSTHESES AND SURGICAL METHOD FOR IMPLANTING INTERVERTEBRAL PROSTHESES, PARTICULARLY FOR PERCUTANEOUS MINIMALLY-INVASIVE SURGICAL PROCEDURES

TECHNICAL FIELD

The present application relates to an intervertebral prosthesis, particularly for percutaneous minimally-invasive surgical procedures, and to the apparatus and surgical method for implanting the intervertebral prosthesis.

BACKGROUND

Numerous disorders affecting the spinal column and in particular affecting the intervertebral discs are currently known in medicine.

Some of these disorders produce a degeneration of the fibrous capsule of the intervertebral disc, which reduces its elasticity and becomes damaged, allowing part of the nucleus pulposus to escape.

This phenomenon is commonly known as "hernia".

There are also other disorders, of a progressive type, which entail the thinning, over time, of the intervertebral disc owing to the loss of its ability to retain water inside it. This thinning often also produces the thinning of the facet capsules, with consequent pain.

In some cases, this thinning can lead to the reduction of the medullary canal, with a severe risk of chronic claudication.

In many cases, progressive deterioration of the intervertebral disc requires the implantation of an intervertebral prosthesis, which substantially replaces said disc.

Among the various known types of intervertebral prosthesis, one is available which has the main function of facilitating the fusion of two adjacent vertebrae.

This type of prosthesis generally comprises one or two bodies made of osteoconductive material which are arranged, by way of a surgical procedure, in mutually opposite positions between the two adjacent vertebrae.

The materials used to provide the two bodies facilitate the growth and adhesion of bone tissue so as to cause the fusion of the two vertebrae, which can no longer move with respect to each other.

This type of conventional intervertebral prosthesis, which is generally applied at the level of the lumbar vertebrae, which are the ones subjected to the greatest load determined by body weight, is not free from drawbacks, which include the fact that generally it requires an extremely invasive surgical procedure for implantation.

The surgeon in fact proceeds by preparing the intervertebral disc to accommodate the intervertebral prosthesis and inserts the prosthesis itself by creating initially a percutaneous anterolateral access of such size as to be able to accommodate a cylindrical retractor instrument, which, once inserted in the patient through said percutaneous anterolateral access, affords a maneuvering channel that is of width comprised generally between six and nine centimeters, is delimited laterally by the retractor instrument, and is fully free from the organic tissues that are present between the access created and the intervertebral disc to be operated on.

In this manner, the surgeon can operate on the disc by working visually and by inserting the various surgical instruments, as well as the prosthesis itself, through the maneuvering channel that has been created.

In greater detail, the method described above involves entry with a first small cylindrical instrument, then cannulas that have the function of expanding the first access, and finally the retractor, which also expands further the first access.

It should be stressed that this surgical procedure, in addition to being inherently laborious and time-consuming, can lead to severe consequences for the patient since, although the procedure is monitored at the neurological level by a device that detects if there is a nervous structure proximate to the surgical instrument, it does not allow the surgeon to detect and therefore monitor the compression of tissues and muscles (against the transverse apophyses) caused by the divarication or expansion of the retractor instrument, which very often leads to the stretching and/or compression of the femoral plexus throughout the duration of the procedure.

This can sometimes lead to temporary dysesthesias of the associated femoral nerve and to paresthesias, motor deficits of the quadriceps, weakness in hip flexion, and in some cases to actual permanent damage of the plexus itself, all the consequences cited above being permanent.

Indeed, recently manufacturers have recommended closing the retractor every ten minutes and waiting another ten minutes before resuming the procedure.

Another drawback of the background art, discussed in some studies, consists in that in a lateral position at the L4-L5 and L3-L4 level the veins and aortas approach the space affected by the procedure.

A further drawback of the background art consists in that it requires the removal also of a portion of annulus that is as wide as the implant that will be positioned in addition to the internal part of the disc (nucleus pulposus), which leads to an incorrect placement of the implant in said disc.

A further drawback of the background art consists in the onset, a short time later, of inguinal hernias caused by the access (tissue stress).

A further drawback of the background art consists in that, if it is necessary to remove the implant owing to infections, incorrect placement or size, et cetera, then surgery to remove and/or replace the implant is highly invasive and complex.

A further drawback of the background art consists in that, if it is necessary to provide posterior stabilization (70% of cases), with the background art first of all lateral access is provided in order to position the implant and then the patient is turned over to perform the arthrodesis procedure via a posterior pathway; this entails removing all the surgical sheets from the patient, repositioning him/her on the operating table, placing the new sheets again with the posterior access and continuing with the procedure. If efficient operating room staff is available, this procedure requires 25 minutes, extending all operating times (anesthesia, etc.).

SUMMARY

The aim of the present invention is to provide an intervertebral prosthesis that is adapted to create a bone bridge between two adjacent vertebrae to be fused, such that it can be implanted in total safety with a percutaneous and minimally-invasive procedure, so as to overcome the limitations and drawbacks of the background art.

Within the scope of this aim, an object of the present invention is to devise a surgical method and to provide an apparatus that allow the implantation of said intervertebral prosthesis in a manner that is simple, fast, effective and most of all reliable.

This aim, as well as these and other objects that will become better apparent hereinafter, are all achieved by an intervertebral prosthesis, particularly for percutaneous minimally-invasive surgical procedures, which comprises an element that has a substantially disc-like shape and is adapted to be inserted between two adjacent vertebrae of a patient in whom said intervertebral prosthesis is to be implanted as a replacement of the intervertebral disc comprised between them, so as to support entirely the vertebral endplates over the largest possible surface and at the same time impart an anteroposterior angle aimed at maintaining physiological lordosis and sagittal balance in order to form a bone bridge between said adjacent vertebrae, wherein said element has a through-hole that passes through said element from side to side and is adapted to slideably accommodate a guiding wire, inserted beforehand in said patient along a direction that is parallel to the sagittal axis of said patient through a percutaneous anterolateral access, for the wire-guided insertion of said intervertebral prosthesis, said through-hole extending along a radial direction with respect to the geometry of said element so that it is oriented, once implanted, along a direction that is substantially perpendicular and parallel, respectively, to the craniocaudal axis of said patient and to said sagittal axis.

Preferably, such element has a threaded hole that is defined at a side wall of said element substantially coaxially to said through-hole, said threaded hole having a larger diameter than said through-hole for its engagement with a threaded shank that is defined at the end of an insertion instrument that is shaped substantially like a cannula so that it can be wire-guided during its insertion in said patient by way of said guiding wire.

Preferably, such element has, at its upper face and at its lower face, which are intended to come into contact with the vertebral endplates of said adjacent vertebrae, a surface provided with a plurality of protruding bodies that are adapted to facilitate the grip of said intervertebral prosthesis on said vertebral endplates of said adjacent vertebrae.

Preferably, such protruding bodies comprise toothed ridges.

Preferably, such element has at least one lightening cavity that passes through said element from said upper face to said lower face.

Preferably, such element has a trabecular structure that is made of osteoconductive material so as to facilitate bone fusion between said intervertebral prosthesis and said adjacent vertebrae.

Furthermore, this aim, as well as these and other objects that will become better apparent hereinafter, are all achieved by an apparatus for implanting intervertebral prostheses, particularly for percutaneous minimally-invasive surgical procedures, which comprises:
an operating table on which the patient to be operated is rested,
surgical instruments required for the surgical procedure,
a radiological device adapted to take radiographs in order to determine the exact position of the intervertebral disc on which to operate and the optimum direction for guiding said surgical instruments,
wherein said apparatus comprises at least one guiding wire that can be inserted in said patient through a percutaneous anterolateral access along a direction that is substantially perpendicular and parallel, respectively, to the craniocaudal axis and to the sagittal axis of said patient, said surgical instruments being slideably associable with said guiding wire in order to perform the surgical procedure in a wire-guided manner.

Preferably, the surgical instruments comprise at least one scalpel at the opening of said percutaneous anterolateral access.

Preferably, the surgical instruments comprise at least one cannulated instrument that is adapted to be inserted in said patient through said percutaneous anterolateral access along a direction that is substantially perpendicular and parallel, respectively, to said craniocaudal axis and to said sagittal axis, said cannulated instrument being beveled at its distal tip so as to avoid damaging any nervous structures that may be present and being provided internally with a plug element that is beveled at its distal tip so as to avoid damaging any nervous structures that may be present and is removable for the insertion of said guiding wire once said cannulated instrument has been positioned proximate to said intervertebral disc.

Preferably, the surgical instruments comprise at least one hernia clamp that is provided with an external cannulation that is slideably associable with said guiding wire in a manner that is eccentric with respect to the longitudinal axis of said at least one hernia clamp for the wire-guided insertion of said at least one hernia clamp in said patient and in order to remove the part of said intervertebral disc that will be replaced by an intervertebral prosthesis, by rotating around said guiding wire.

Preferably, the surgical instruments comprise at least one cannulated rasp that is slideably associable with said guiding wire for its wire-guided insertion in said patient so as to be able to remove the cartilage of the vertebral endplates that are adjacent to said intervertebral disc and cause them to bleed so as to facilitate bone fusion between said intervertebral prosthesis and said vertebral endplates.

Preferably, the at least one cannulated rasp is of the motorized type.

Preferably, the surgical instruments comprise at least one cannulated measurer, which can be slideably associated with said guiding wire for its wire-guided insertion in said patient in such a manner as to be able to determine the height of said intervertebral prosthesis to be implanted.

Preferably, the cannulated measurer has, at its distal part, substantially the shape of a parallelepiped with radiused edges and a substantially rectangular transverse cross-section, so that it is inserted in said intervertebral disc, where said intervertebral prosthesis will be positioned, with its lesser transverse thickness oriented substantially along said craniocaudal axis, said cannulated measurer being able to rotate about said guiding wire in such a manner as to be able to restore the intervertebral space between said intervertebral endplates by placing said cannulated measurer with its greater transverse thickness oriented substantially along said craniocaudal axis following a 90° rotation of said cannulated measurer.

Preferably, the surgical instruments comprise at least one insertion instrument that can be associated, at its distal part, with said intervertebral prosthesis to be implanted, is substantially shaped like a cannula and can be slideably associated with said guiding wire for its wire-guided insertion in said patient so as to be able to correctly position said intervertebral prosthesis, said at least one insertion instrument being disengageable from said intervertebral prosthesis so that it can be removed once said intervertebral prosthesis has been placed in said intervertebral space.

Preferably, the at least one insertion instrument has, at said distal part thereof, a threaded shank that can engage a threaded hole, which is defined in said intervertebral prosthesis at a side wall of said intervertebral prosthesis substantially coaxially to a through-hole that passes through said intervertebral prosthesis from side to side along a direction parallel to said sagittal axis and is adapted to slideably accommodate said guiding wire, so as to be able to transversely move said intervertebral prosthesis within said intervertebral space and so that it can be unscrewed from said intervertebral prosthesis so that it can be removed from said patient, said threaded hole having a larger diameter than said through-hole.

Preferably, the surgical instruments comprise at least one milling tool that can be inserted in said patient through said percutaneous anterolateral access and is adapted to create a hole that passes through any bone structures that interfere with the operating trajectory.

Preferably, an articulated arm is comprised which can be fixed to said operating table or to the spinous process of said patient or to the bars of the arthrodesis, if they are present, said articulated arm being provided, at its movable end, with a guiding element that is adapted to support and guide said surgical instruments and to support said guiding wire during the surgical procedure, said guiding element being positionable by way of said articulated arm with respect to said intervertebral disc to be operated on at least along three degrees of freedom that are substantially parallel respectively to said craniocaudal axis, to said sagittal axis and to the latero-lateral axis of said patient.

Preferably, the articulated arm is of the motorized type.

Preferably, a neurological device is comprised which has one pole that can be connected electrically to said surgical instruments and the other pole that can be connected to the nervous system of said patient so as to warn the surgeon if the surgical instrument being used is proximate to the nervous structures of said patient.

Furthermore, this aim, as well as these and other objects that will become better apparent hereinafter, are all achieved by a surgical method for implanting intervertebral prostheses, particularly for percutaneous minimally-invasive surgical procedures, comprising:

placing a patient to be operated on, on an operating table, taking a first radiograph by way of a radiological device in order to establish the exact position of the intervertebral disc to be operated on, opening a percutaneous anterolateral access by way of a scalpel, inserting in said patient, through said percutaneous anterolateral access, a series of surgical instruments that are adapted to prepare said intervertebral disc to accommodate an intervertebral prosthesis, inserting said intervertebral prosthesis in said patient through said percutaneous anterolateral access, wherein said insertion steps are performed with the aid of a guiding wire, inserted previously in said patient through said percutaneous anterolateral access along a direction that is substantially perpendicular and parallel, respectively, to the craniocaudal axis and to the sagittal axis of said patient, said surgical instruments and said intervertebral prosthesis being slideably associable with said guiding wire in order to perform the surgical procedure in a wire-guided manner.

Preferably, before the insertion steps, an articulated arm is fixed to said operating table or to the spinous process of said patient or to the bars of the arthrodesis, if they are present, in such a manner as to position a guiding element, with which said articulated arm is provided, which is adapted to support and guide said surgical instruments and to support said guiding wire during the surgical procedure, said guiding element defining an operating trajectory that is oriented along a direction that is substantially perpendicular and parallel, respectively, to said craniocaudal axis and to said sagittal axis.

Preferably, prior to the step of insertion of said series of surgical instruments and if there are bone structures present that interfere with the operating trajectory imposed by said guiding element in the direction of said intervertebral disc, the following are performed:

the insertion of at least one milling tool, in a guided manner by way of said guiding element through said percutaneous anterolateral axis, the milling of said bone structure to create a passage through which said cannulated instrument is to be inserted, the extraction of said at least one milling tool through said percutaneous anterolateral access.

Preferably, the step of insertion of said series of surgical instruments comprises:

the insertion of at least one cannulated instrument, provided internally with a removable plug element, until said intervertebral disc is reached, said at least one cannulated instrument and said plug element being beveled at their distal tips so as to avoid damaging any nervous structures that may be present, said at least one cannulated instrument being inserted with the aid of said guiding element along said operating trajectory, the removal of said plug element, the insertion of said guiding wire in said cannulated instrument and the penetration of said intervertebral disc by said guiding wire for a depth that is less than the transverse thickness of said intervertebral disc, the extraction of said cannulated instrument through said percutaneous anterolateral access, slipping it off said guiding wire, which remains stationary.

Preferably, the step of insertion of said series of surgical instruments comprises:

the wire-guided insertion of at least one hernia clamp provided with an external cannulation that can be slideably associated with said guiding wire in an eccentric manner with respect to the longitudinal axis of said at least one hernia clamp, the removal of part of said intervertebral disc with the aid of said at least one hernia clamp with rotation of said at least one hernia clamp around said guiding wire to create a seat for accommodating said intervertebral prosthesis which is delimited by the vertebral endplates that are adjacent to said intervertebral disc, the extraction of said at least one hernia clamp through said percutaneous anterolateral access, slipping it off said guiding wire, which remains stationary.

Preferably, the step of insertion of said series of surgical instruments comprises:

the wire-guided insertion of at least one cannulated rasp, the removal, with the aid of said at least one cannulated rasp, of the cartilage of said vertebral endplates with bleeding thereof in such a manner as to facilitate bone fusion between said intervertebral prosthesis and said vertebral endplates, the extraction of said at least one cannulated rasp through said percutaneous anterolateral access, slipping it off said guiding wire, which remains stationary.

Preferably, the step of insertion of said series of surgical instruments comprises:

the wire-guided insertion, where said intervertebral prosthesis will be positioned, and wire-guided extraction of a series of cannulated measurers of different sizes, having a shape, at their distal part, that is substantially parallelepiped with radiused edges and a substantially rectangular transverse cross-section, in succession with respect to each other in such a manner as to be able to determine the height of said intervertebral prosthesis to be implanted, said cannulated measurers being inserted, in said intervertebral disc, with their lesser transverse thickness oriented substantially along said craniocaudal axis, if a compression of said intervertebral disc has occurred, the rotation through 90° of one of said cannulated measurers in such manner as to position it with its greater transverse thickness oriented substantially along said craniocaudal axis, for the mutual spacing apart of said vertebral endplates, with the consequent restoring of the intervertebral space between said intervertebral endplates, the extraction of said cannulated measurer through said percutaneous anterolateral access, slipping it off said guiding wire, which remains stationary.

Preferably, the step of insertion of said intervertebral prosthesis comprises:

the wire-guided insertion of at least one insertion instrument that supports, at its distal part, said intervertebral prosthesis in such a manner as to correctly position said intervertebral prosthesis in said previously prepared intervertebral space, said intervertebral prosthesis being wire-guided and being associated detachably with said at least one insertion instrument by shape mating, the disengagement of said at least one insertion instrument from said intervertebral prosthesis, with said intervertebral prosthesis arranged within said intervertebral space, for the extraction of said at least one insertion instrument and of said guiding wire.

Preferably, the steps of insertion and/or extraction of said milling tool, of said series of surgical instruments and of said intervertebral prosthesis are at least partially monitored by way of second radiographs taken with the aid of said radiological device.

Preferably, in the steps of insertion and/or extraction of said milling tool, of said series of surgical instruments and of said intervertebral prosthesis, at least said milling tool and said at least one cannulated instrument are connected electrically to one pole of a neurological device, the other pole of said neurological device being connected electrically to the nervous system of said patient in such a manner as to warn the surgeon if said surgical instrument being used is proximate to the nervous structures of said patient.

Further characteristics and advantages of the invention will become better apparent from the description of a preferred but not exclusive embodiment of an intervertebral prosthesis, of an apparatus for implanting intervertebral prostheses and of a surgical method for implanting intervertebral prostheses, particularly for percutaneous minimally-invasive surgical procedures, according to the invention, which are illustrated by way of non-limiting example in the accompanying drawings.

DETAILED DESCRIPTION

Figure 1:
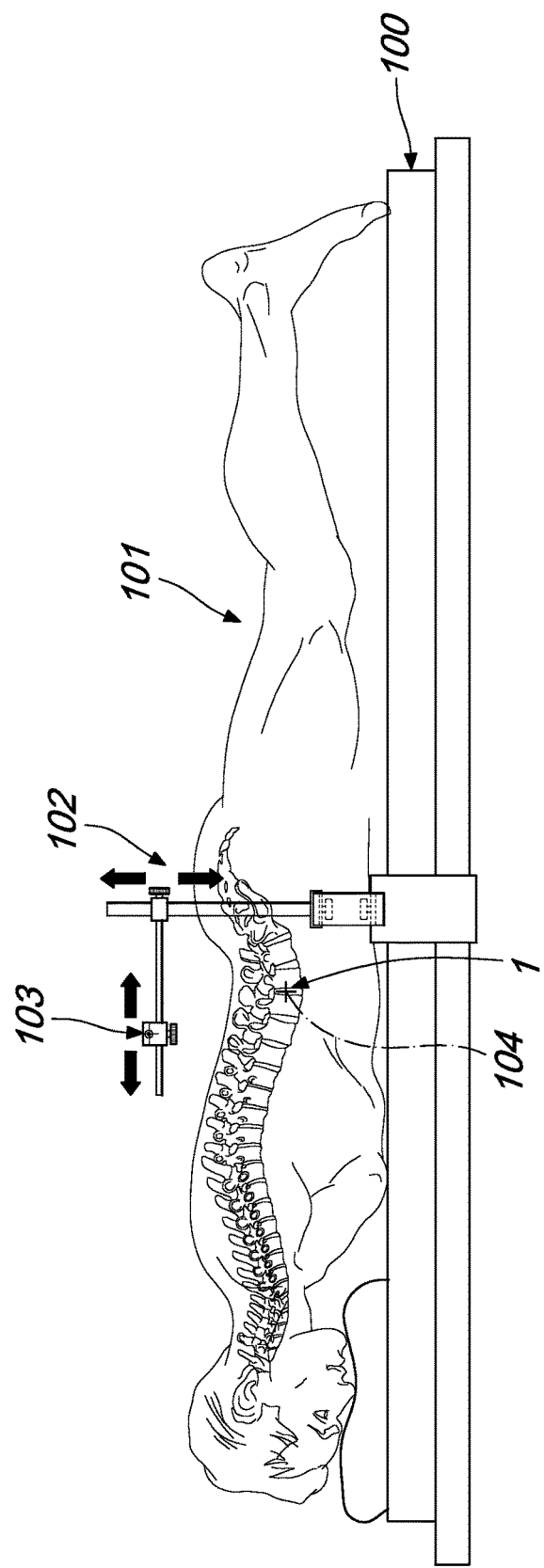
FIGS. 1 to 3 are three views, respectively a side elevation view, a plan view from above and a perspective view, of a schematic representation of the articulated arm that supports the guiding element, according to the present invention, during its positioning with respect to a patient lying prone on an operating table.
Figure 2:
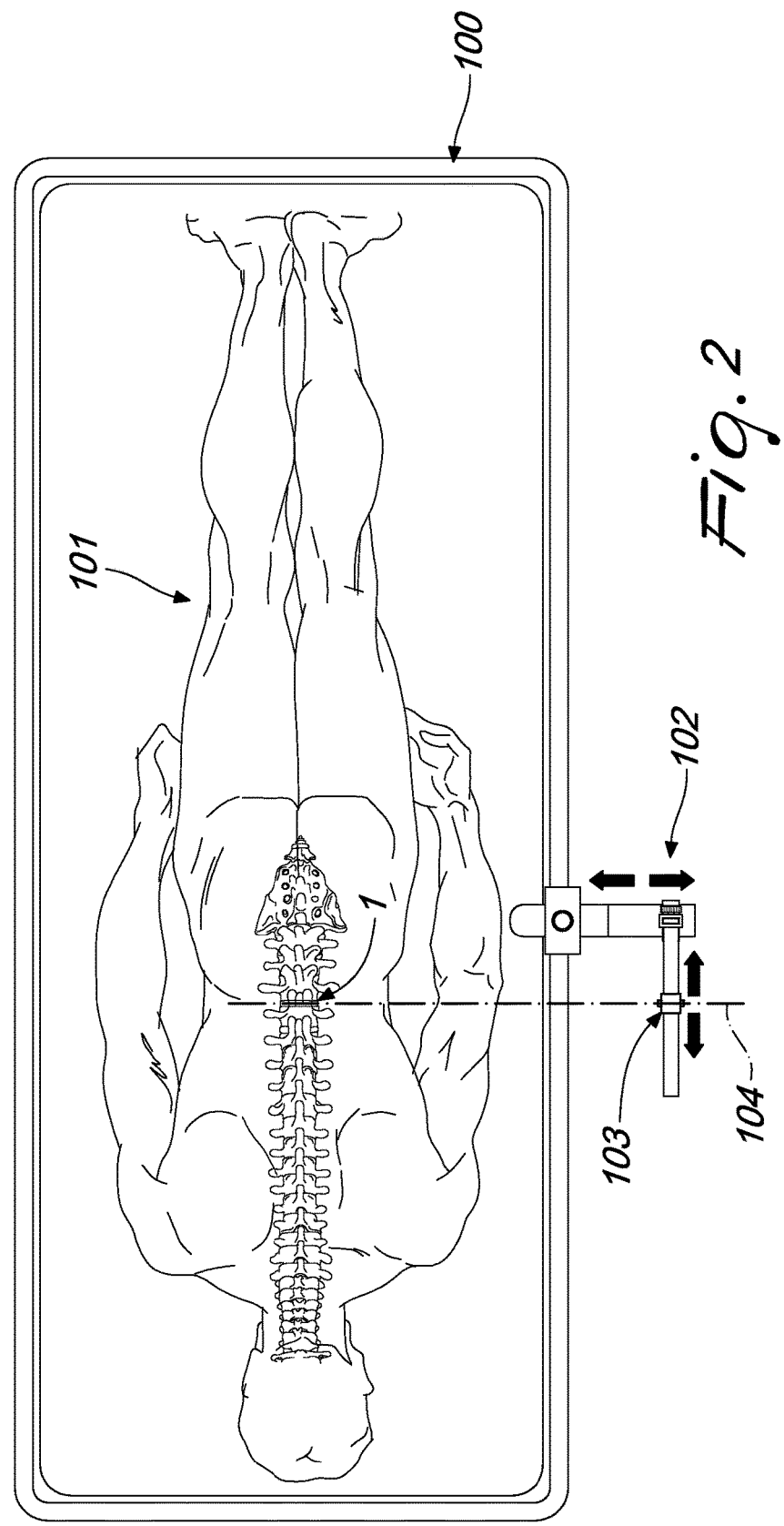
Figure 3:
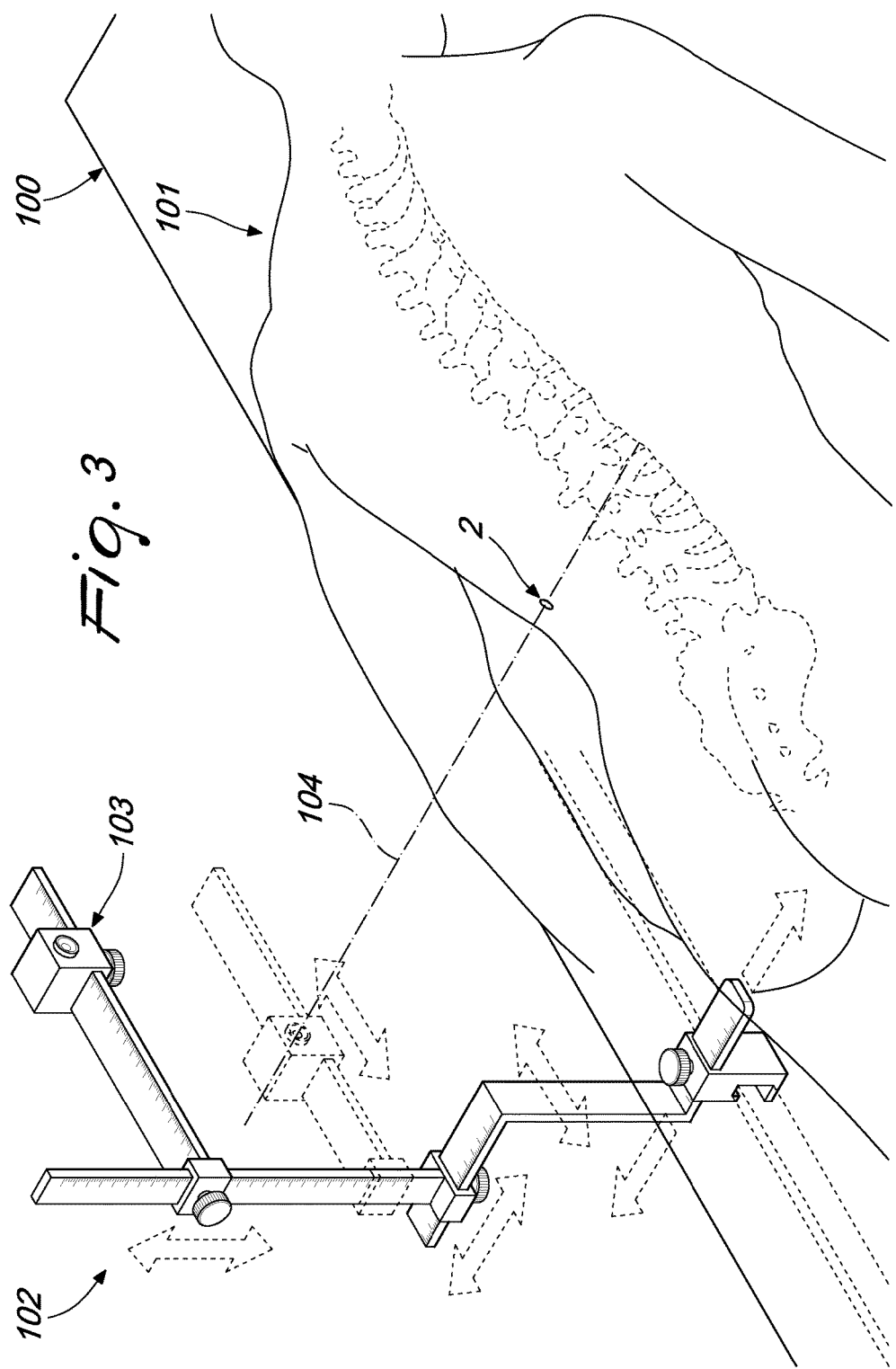
Figure 4:
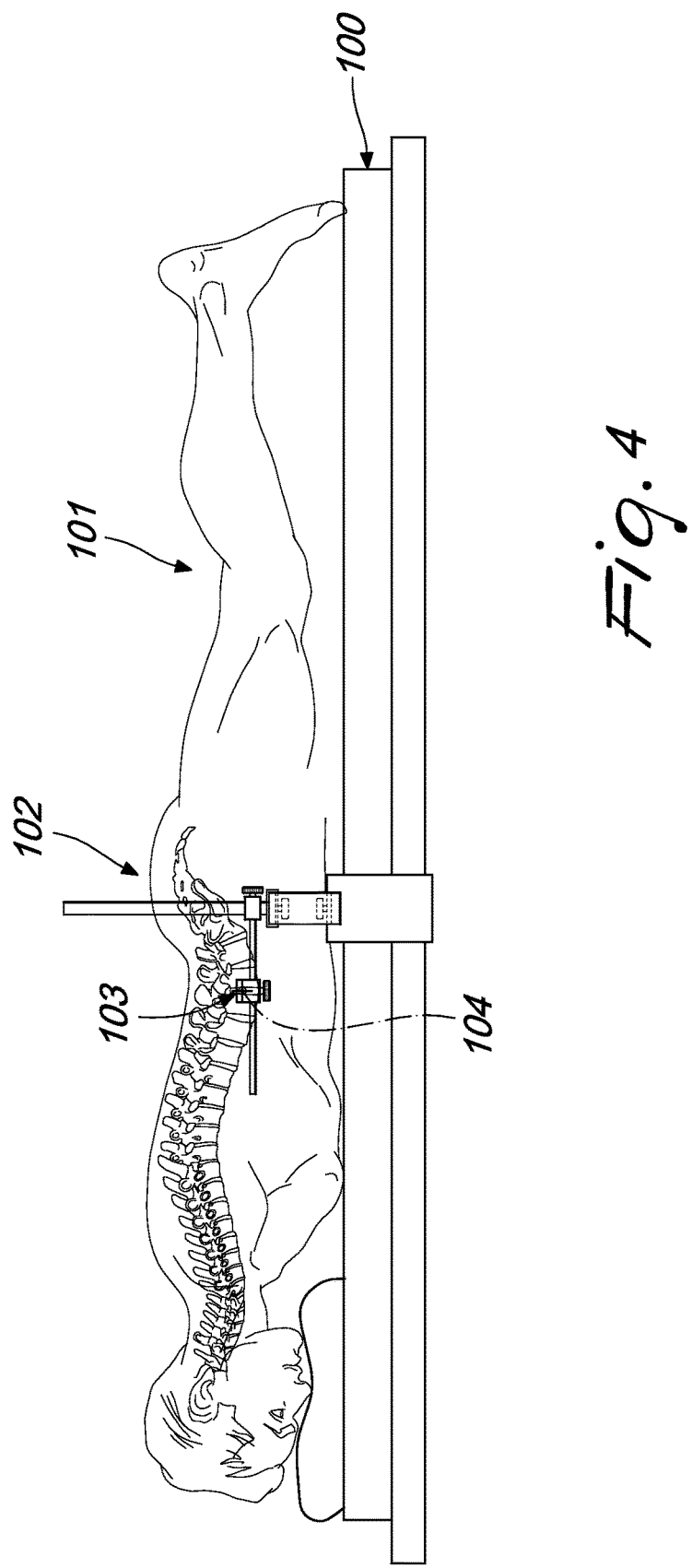
FIG. 4 is a side elevation view of the articulated arm, shown in the preceding figures, after positioning has been performed with respect to a patient lying prone on the operating table.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

With reference to the figures, the surgical method for implanting intervertebral prostheses, particularly for percutaneous minimally-invasive surgical procedures, comprises first of all the placement on an operating table 100 of a patient 101 to be operated on, preferably in a prone position.

Then a first radiograph is performed by way of a radiological device, not shown for the sake of graphical simplicity, in order to establish the exact position of the intervertebral disc 1 to be operated on.

This radiological device, which is per se known and therefore is not described in detail, can comprise for example an image intensifier with a video post or a C-shaped arch with which multiple radiological shots from multiple angles are taken.

Once the point to be operated on has been identified, as shown in FIGS. 1 to 4, an articulated arm 102, for example of the motorized type or of the manual type with sliders, is positioned with respect to the operating table 100 so as to arrange a guiding element 103, with which the articulated arm 102 is provided, along a trajectory 104 that is oriented along a direction that is substantially perpendicular and parallel, respectively, to the craniocaudal axis and to the sagittal axis of the patient 101 and, at this point, one proceeds with the opening of a percutaneous anterolateral access by way of a scalpel 2.

As an alternative, such articulated arm 102 can be fixed to the spinous process of the patient 101 or to the bars of the arthrodesis, if they are present.

In greater detail, the guiding element 103, which is supported by the articulated arm 102 at the movable end of the of the latter, can thus be positioned by way of the articulated arm 103 with respect to the intervertebral disc 1 to be operated on at least along three degrees of freedom that are substantially parallel, respectively, to the craniocaudal axis, to the sagittal axis and to the latero-lateral axis of the patient 101.

One then proceeds with the insertion in the patient 101, through the percutaneous anterolateral access 2, of a series of surgical instruments that are adapted to prepare the intervertebral disc 1 to accommodate an intervertebral prosthesis 3, as well as of an intervertebral prosthesis 3.

According to the invention, these steps of insertion, which involve the aid of the guiding element 103 in order to support and guide the surgical instruments required for the surgical procedure during its execution, are performed with the aid of a guiding wire 105, also supported by the guiding element 103, inserted previously in the patient 101 through the percutaneous anterolateral access 2 along a direction that is substantially perpendicular and parallel, respectively, to the craniocaudal axis and to the sagittal axis of the patient 101, i.e., along the operating trajectory 104 described earlier.

Accordingly, as will be described in greater detail hereinafter, the above mentioned surgical instruments and the intervertebral prosthesis 3 itself are slideably associable with the guiding wire 105 in order to perform the surgical procedure in a wire-guided manner.

Figure 5:
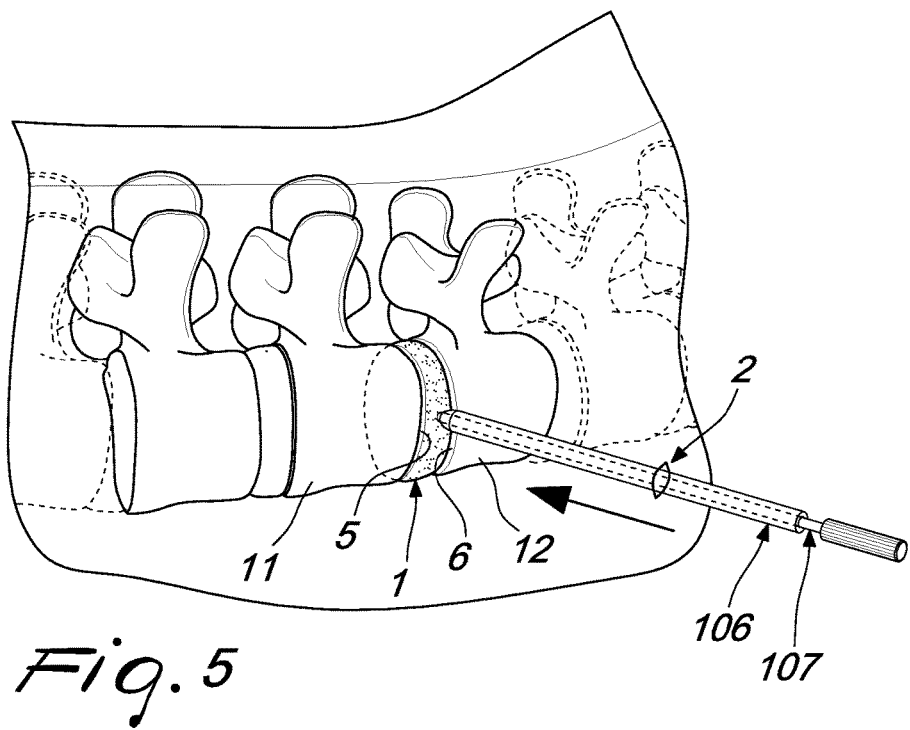
FIGS. 5 and 6 are two views, respectively a perspective view and a plan view from above, of a representation of the step of insertion of a cannulated instrument provided with a plug element, according to the present invention.
Figure 6:
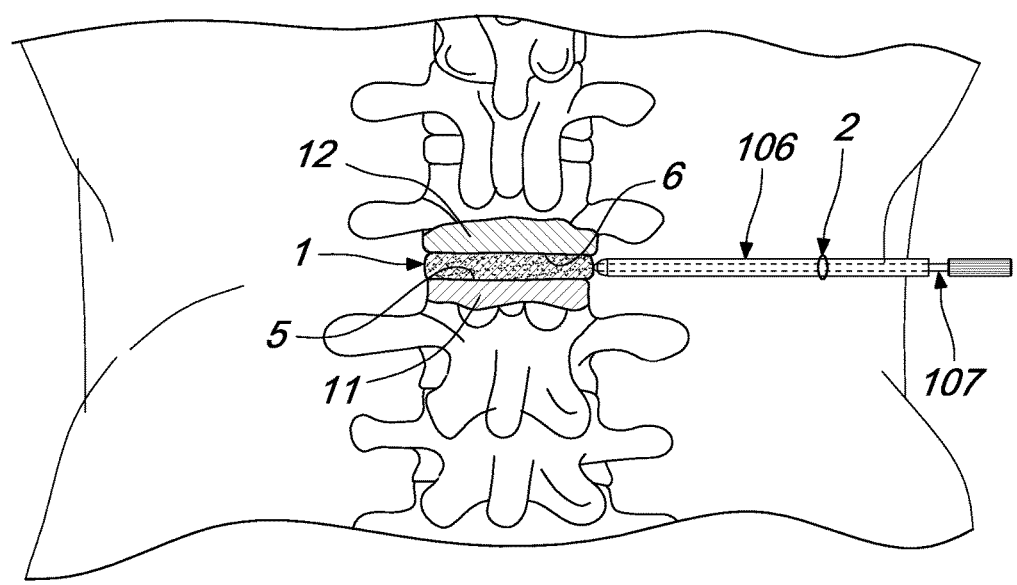
Figure 7:
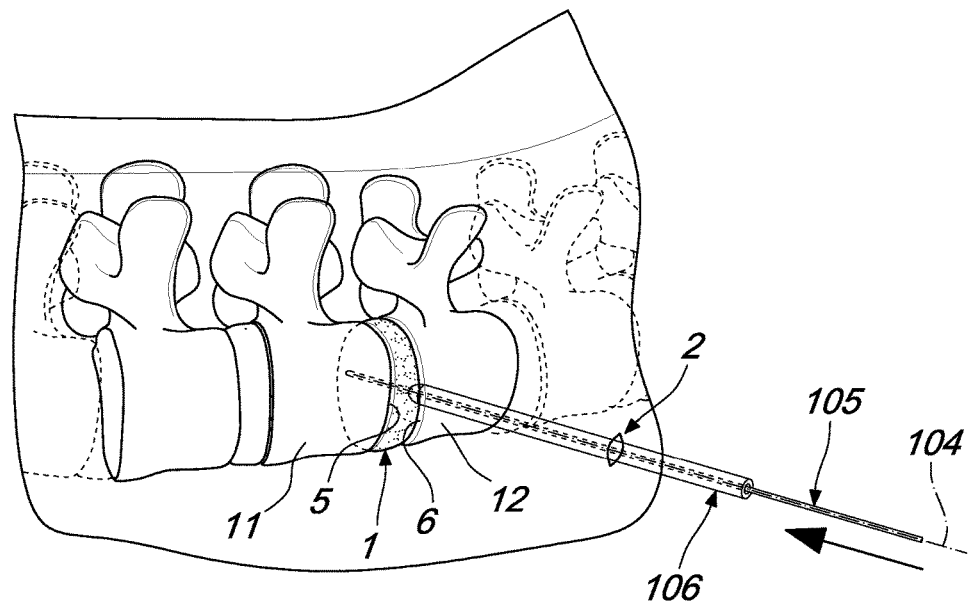
FIGS. 7 and 8 are two views, respectively a perspective view and a plan view from above, of a representation of the step of insertion of a guiding wire in the cannulated instrument, according to the present invention, until the intervertebral disc to be operated on is penetrated.

In greater detail, as in FIGS. 5 and 6, the step of insertion of the surgical instruments comprises the insertion of at least one cannulated instrument 106, which is provided internally with a removable plug element 107, until the intervertebral disc 1 is reached.

Figure 8:
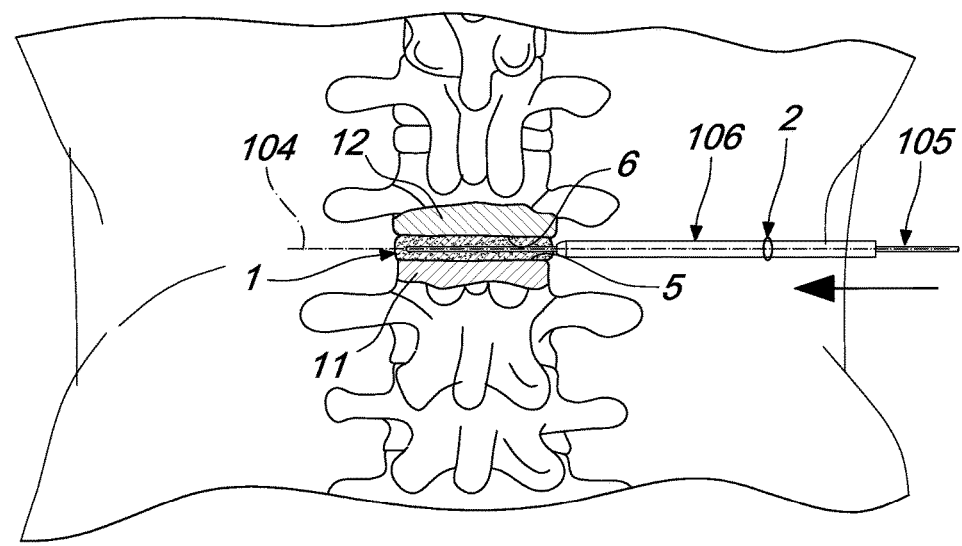

One then moves on to the removal of the plug element 107 in order to be able to insert, as shown in FIGS. 6 and 8, the guiding wire 105 in the cannulated instrument 106 and penetrate the intervertebral disc 1 to a depth that is shallower than the transverse thickness of the intervertebral disc 1.

Figure 9:
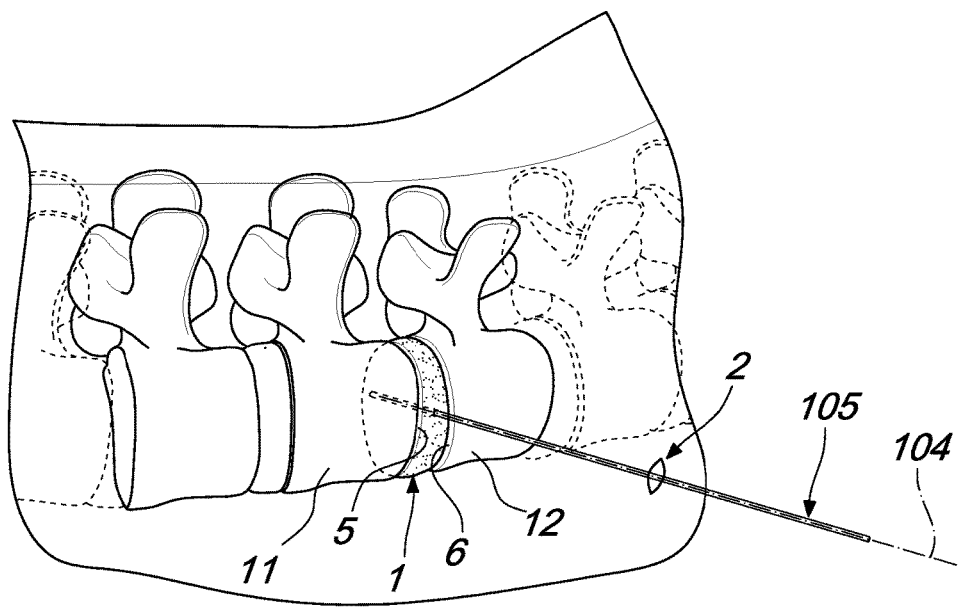
FIG. 9 is a perspective view of the guiding wire, shown in the preceding figures, positioned inside the patient, according to the present invention, once the cannulated instrument has been removed.

Once the guiding wire 105 has been inserted, the cannulated instrument 106 is extracted through the percutaneous anterolateral access 2, slipping it off the guiding wire 105, which remains stationary along the operating trajectory 104, as shown in FIG. 9.

Advantageously, the cannulated instrument 106 and the plug element 107 are beveled at their distal tips 108 so as to avoid damaging any nervous structures that may be present.

Figure 10:
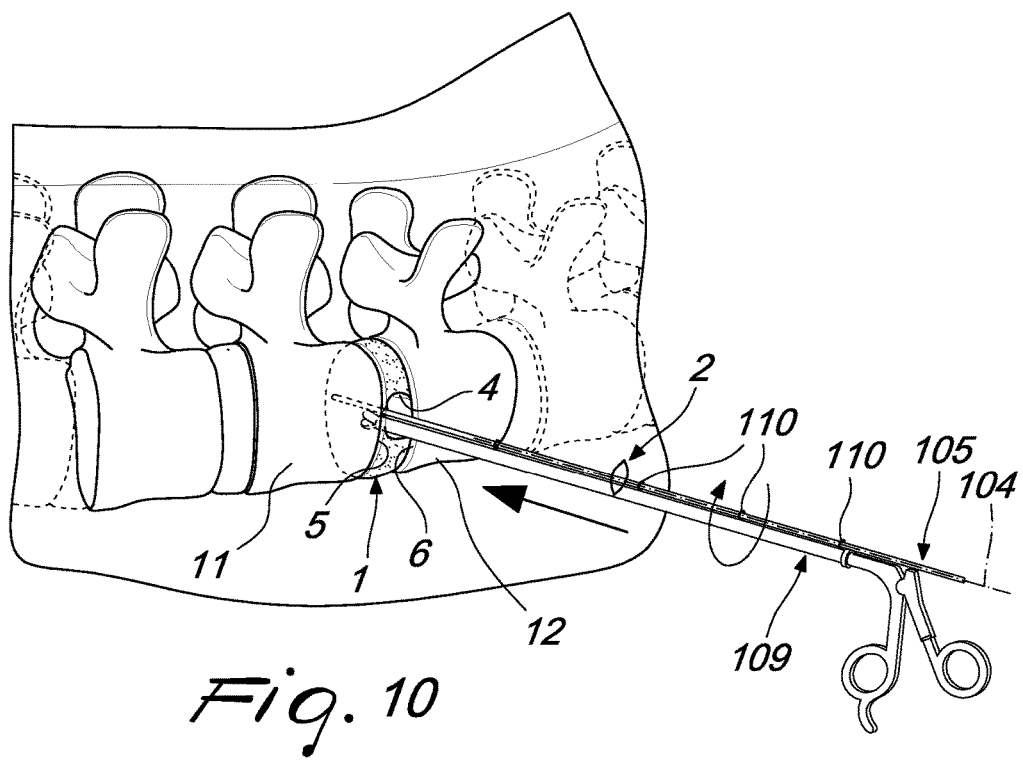
FIGS. 10 to 12 are three views, respectively a perspective view, a plan view from above and another perspective view, of a representation of the step of wire-guided insertion of a hernia clamp and of the step of removal of part of the intervertebral disc, according to the present invention.
Figure 11:
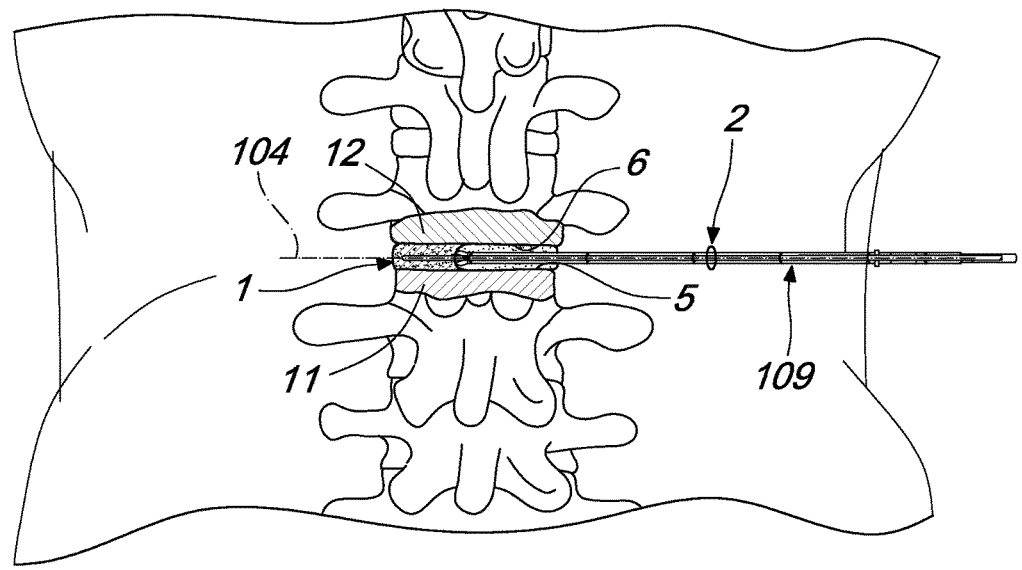
Figure 12:
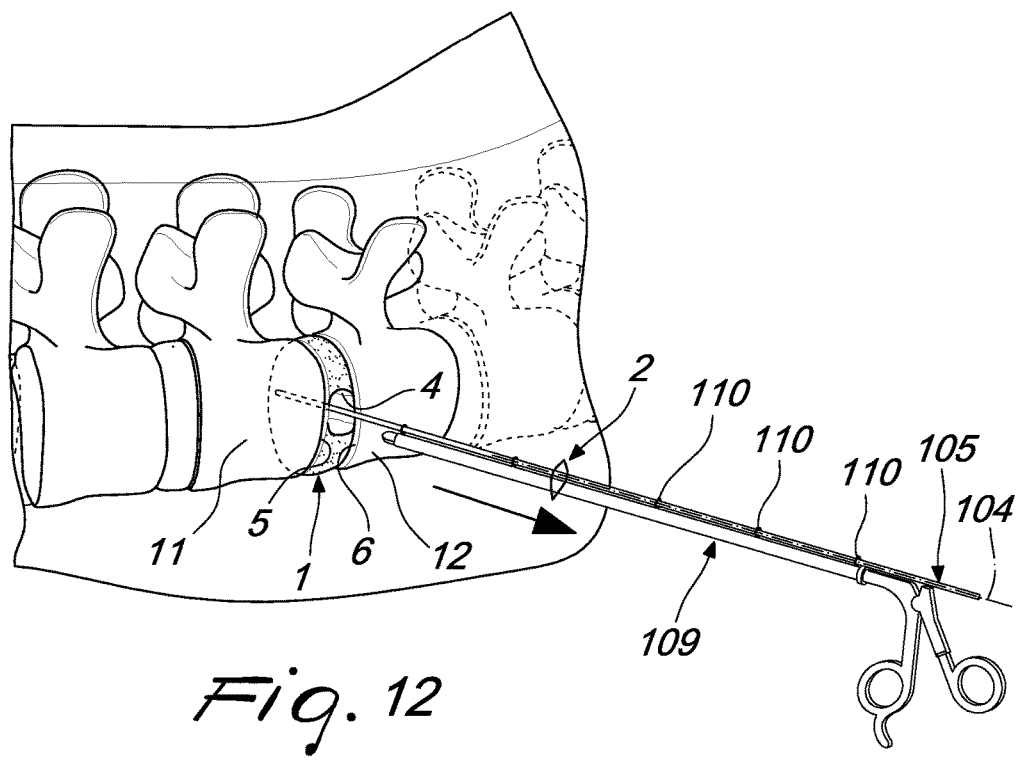

Then, as shown in FIGS. 10 to 12, one proceeds with the wire-guided insertion of at least one hernia clamp 109 provided with an external cannulation 110 that can be slideably associated with the guiding wire 105 eccentrically with respect to the longitudinal axis of said hernia clamp 109.

Advantageously, by virtue of the ability to rotate and translate around and along the guiding wire 105, with the hernia clamp 109 it is possible to proceed to remove part of the intervertebral disc 1 in order to create a seat 4 for accommodating the intervertebral prosthesis 3 that is delimited by the vertebral endplates 5 and 6 that are adjacent to the intervertebral disc 1.

Once the operation has taken place, one proceeds with the extraction of the hernia clamp 109 through the percutaneous anterolateral access 2, slipping it off the guiding wire 105, which remains stationary along the operating trajectory 104.

Figure 13:
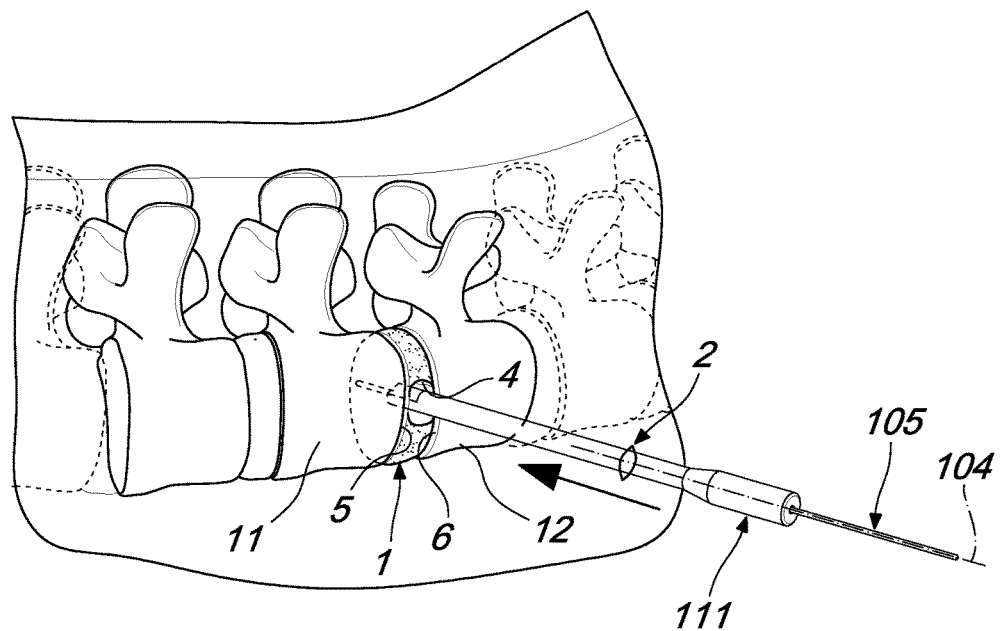
FIGS. 13 to 15 are three views, respectively a perspective view, a plan view from above and another perspective view, of a representation of the step of wire-guided insertion of a cannulated rasp and of the step of removal of the cartilage of the vertebral endplates with bleeding thereof, according to the present invention.
Figure 14:
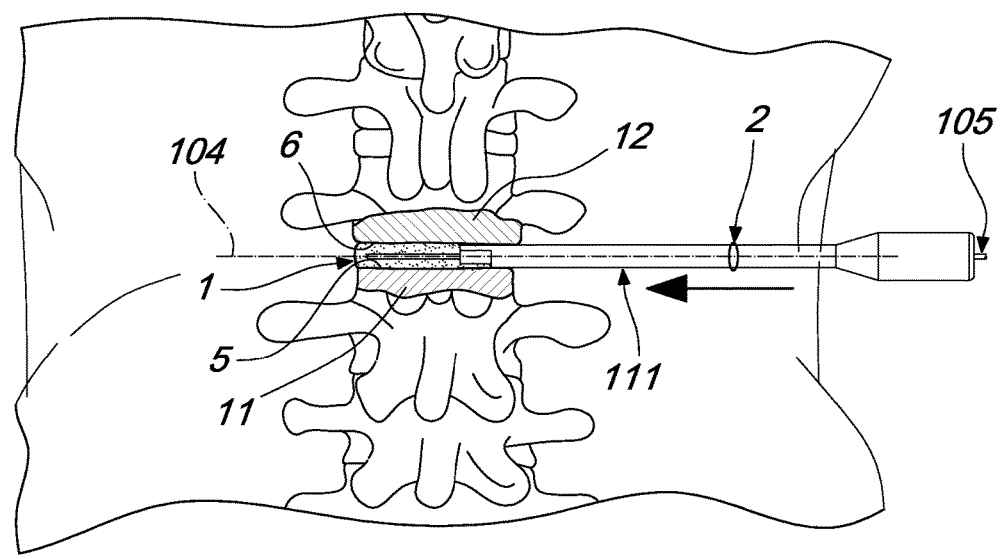
Figure 15:
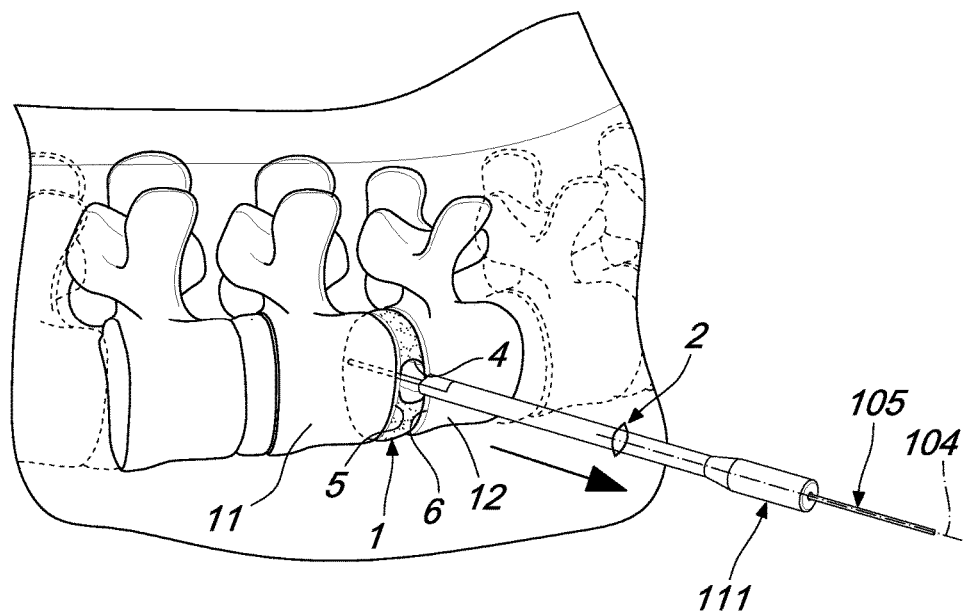

Then, as shown in FIGS. 13 to 15, one proceeds with the wire-guided insertion of at least one cannulated rasp 111, for example of the motorized type, in order to be able to remove the cartilage of the vertebral endplates 5 and 6 with bleeding thereof so as to facilitate bone fusion between the intervertebral prosthesis 3 and the vertebral endplates 5 and 6.

Once the operation has taken place, one proceeds with the extraction of the cannulated rasp 111 through the percutaneous anterolateral access 2, slipping it off the guiding wire 105, which remains stationary along the operating trajectory 104.

Figure 16:
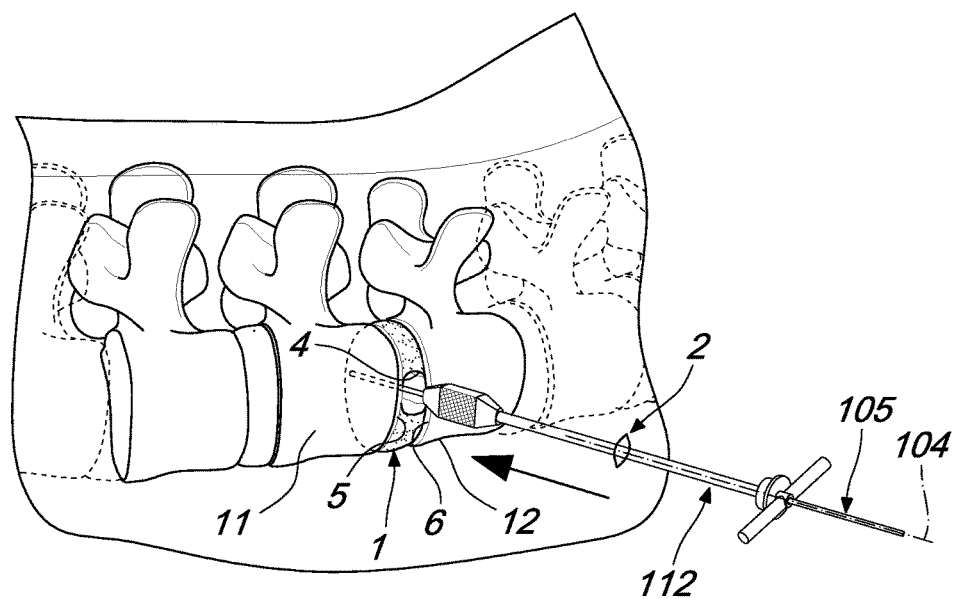
FIGS. 16 to 18 are three views, respectively a perspective view, a plan view from above and another perspective view, of a representation of the step of wire-guided insertion of a cannulated measurer in the intervertebral disc in order to determine the height of the intervertebral prosthesis to be implanted.
Figure 17:
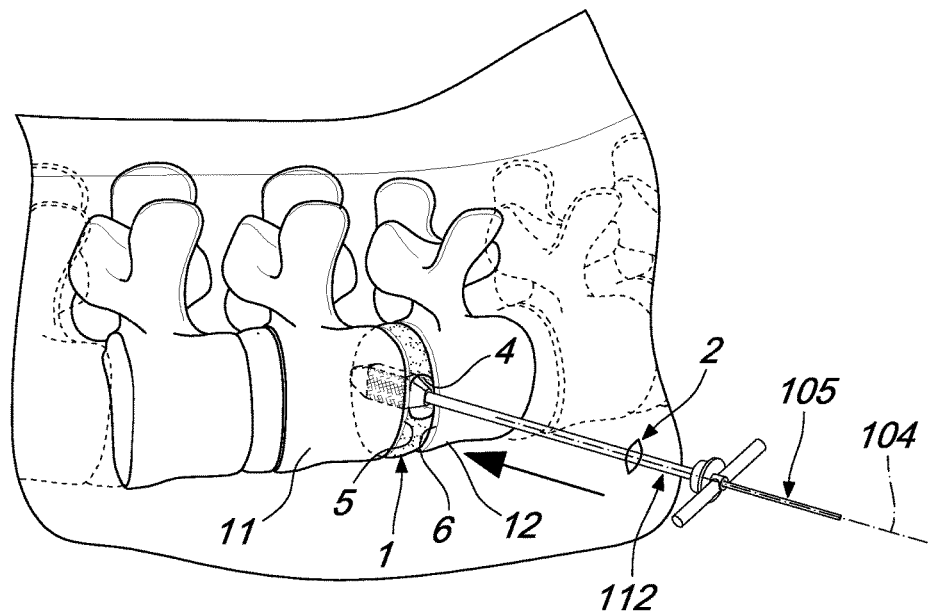
Figure 18:
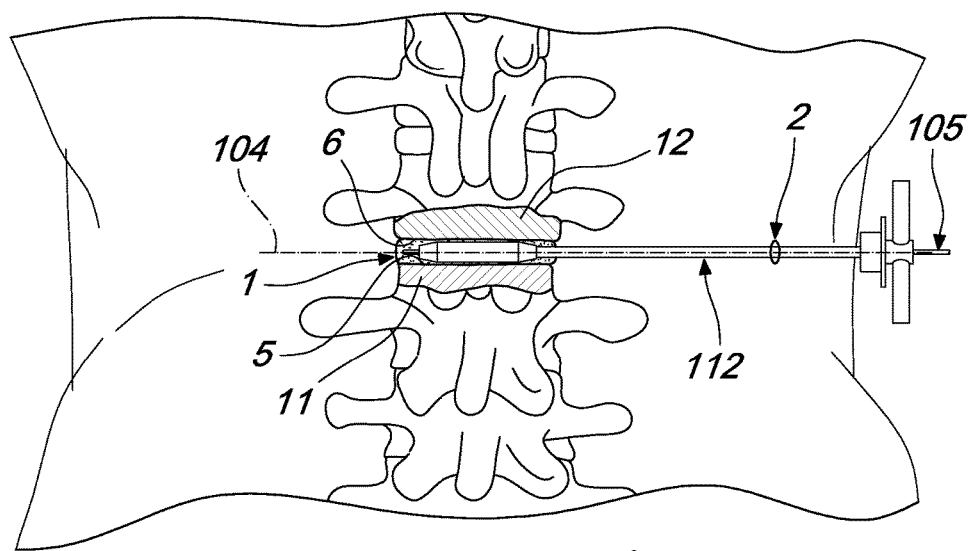

Then, as shown in FIGS. 16 to 18, one proceeds with the wire-guided insertion, where the intervertebral prosthesis 3 will be positioned, and with the wire-guided extraction of said series of cannulated measurers 112 of different sizes, which have, at their distal part, substantially the shape of a parallelepiped with radiused edges and a substantially rectangular transverse cross-section, in sequence with respect to each other so as to be able to determine the height of the intervertebral prosthesis 3.

Figure 19:
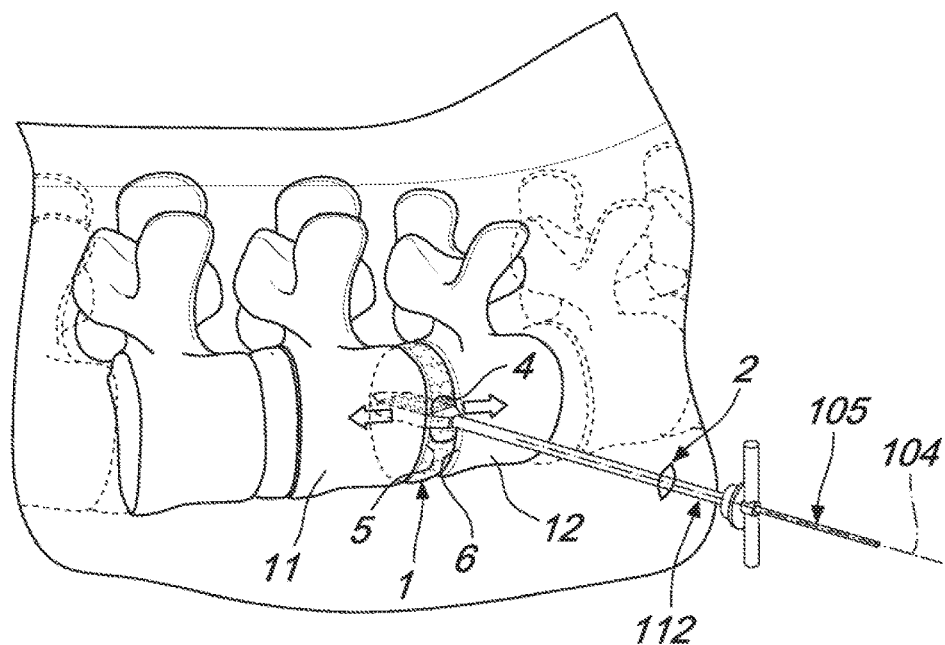
FIGS. 19 and 20 are two views, respectively a perspective view and a plan view from above, of a representation of the step of restoring the intervertebral space between the intervertebral endplates, according to the present invention, by way of the cannulated measurer shown in the preceding figures.
Figure 20:
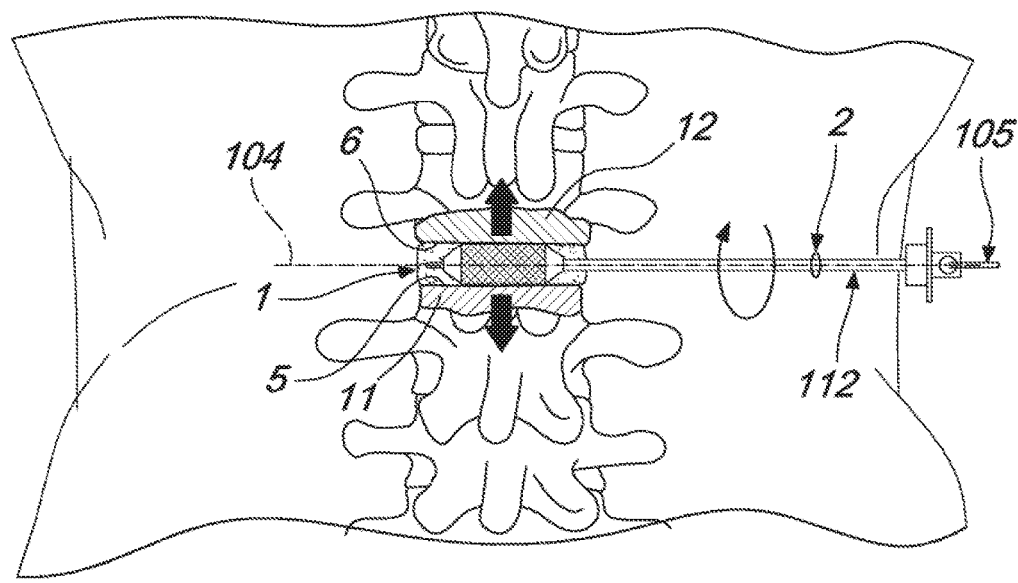
Figure 21:
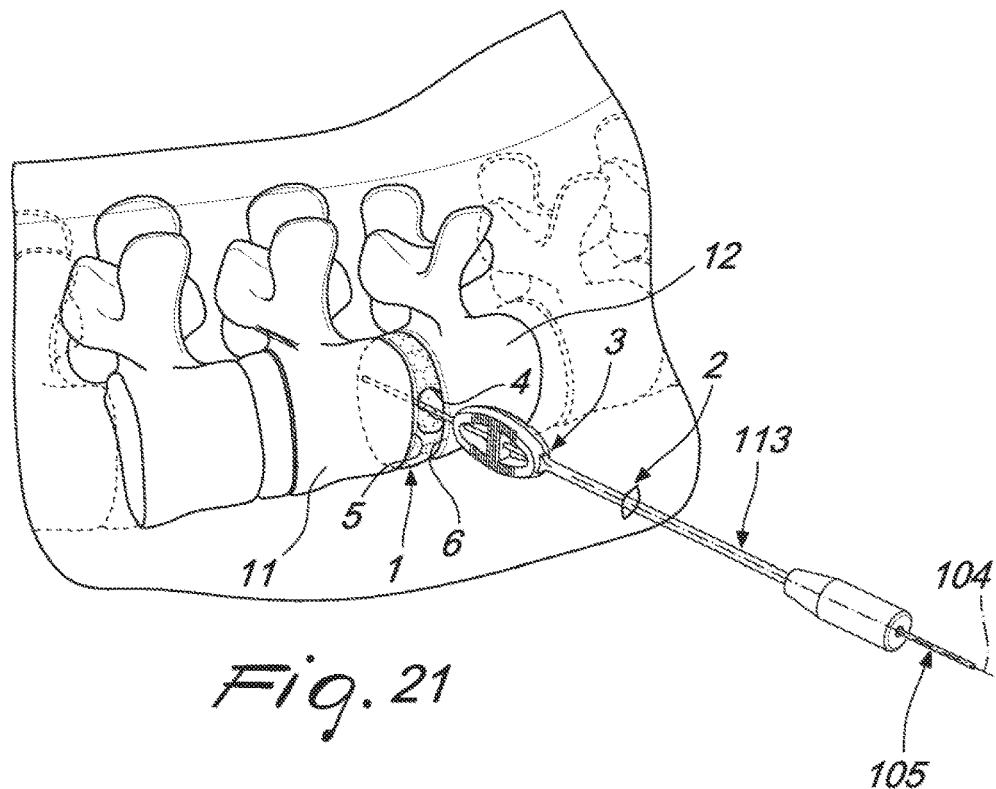
FIGS. 21 to 23 are three views, of which the first one is a perspective view and the subsequent ones are plan views from above, of a representation of the step of wire-guided insertion of an intervertebral prosthesis, according to the present invention, by way of an insertion instrument.
Figure 22:
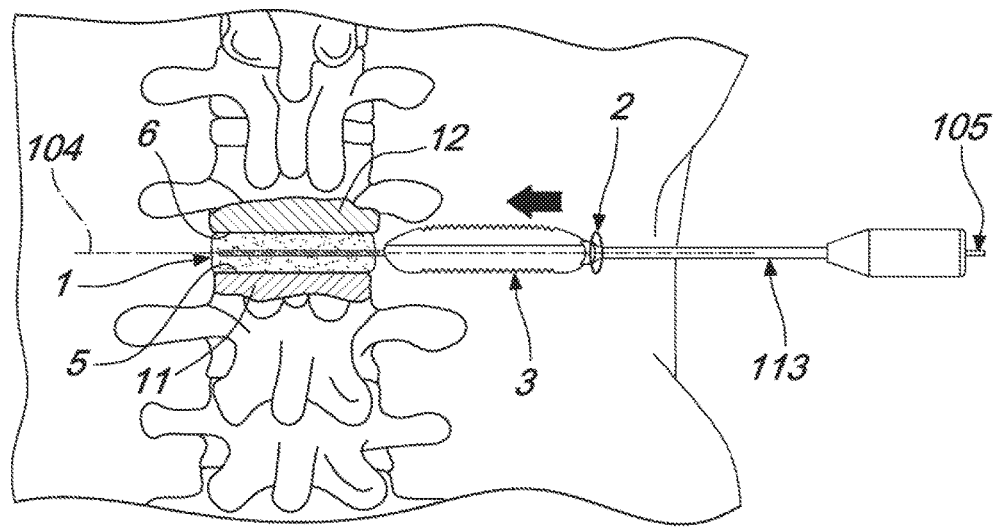
Figure 23:
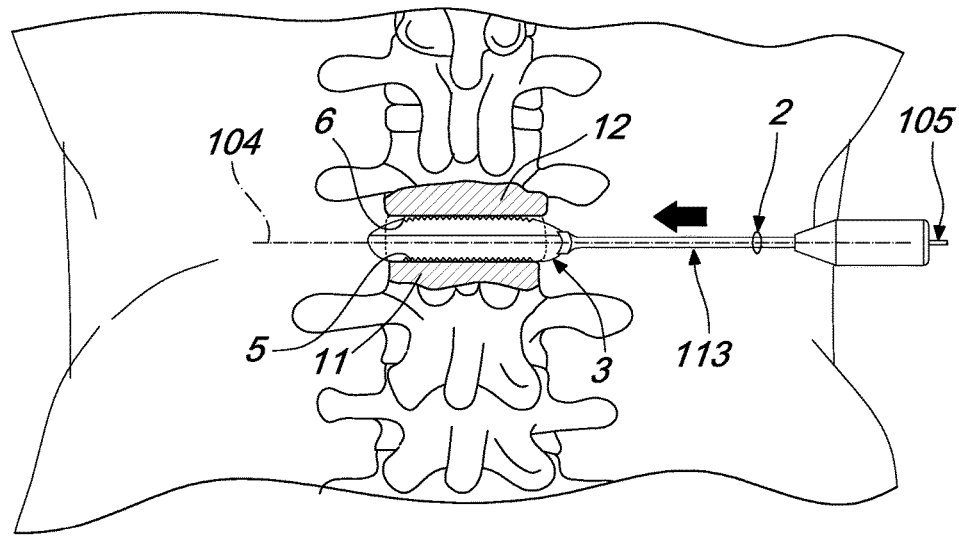

These cannulated measurers 112 are inserted, in the intervertebral disc 1, preferably so that their lesser transverse thickness is substantially oriented along the craniocaudal axis of the patient 101, so that if a compression of the intervertebral disc 1 has occurred, following a 90° rotation of one of the cannulated measurers 112 as shown in FIGS. 19 and 20, it can be positioned so that its greater transverse thickness is substantially oriented along the craniocaudal axis of the patient 101 for the mutual spacing apart of the vertebral endplates 5 and 6, with consequent restoring of the intervertebral space between said intervertebral endplates 5 and 6.

Once the operation has taken place, one proceeds with the extraction of the cannulated measurer 112 through the percutaneous anterolateral access 2, slipping it off the guiding wire 105, which remains stationary along the operating trajectory 104.

Then, as shown in FIGS. 21 to 28, one proceeds with the wire-guided insertion of at least one insertion instrument 113 which carries, at its distal part, the intervertebral prosthesis 3 in such a manner as to position it correctly in the previously prepared intervertebral space.

In greater detail, the intervertebral prosthesis 3, which as will be described in greater detail hereinafter is of the wire-guided type, is associated detachably with the insertion instrument 113 by shape mating so that it can be disengaged from the insertion instrument 113, once it has been placed within the intervertebral space, for the extraction of the insertion instrument 113 and of the guiding wire 105.

Figure 29:
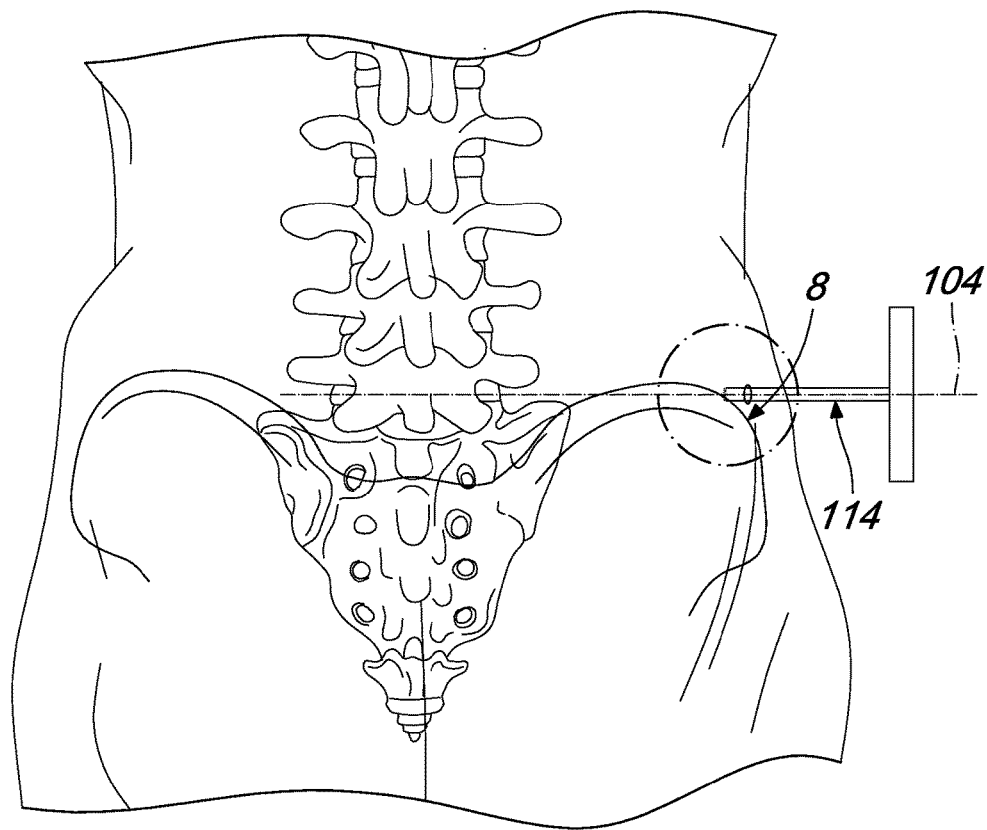
FIG. 29 is a plan view from above of a representation of the milling step of a milling tool, in a guided manner by way of the guiding element shown in the preceding figures, in order to create a passage through which said cannulated instrument is to be inserted.
Figure 30:
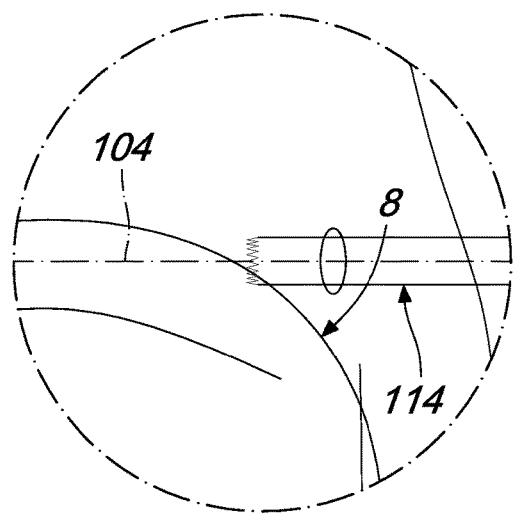
FIG. 30 is an enlarged-scale view of a detail of the milling tool shown in FIG. 29.

As shown in FIGS. 29 and 30, if there are bone structures 8 that interfere with the operating trajectory 104 imposed by the guiding element 103 in the direction of the intervertebral disc 1, such as for example the iliac crest, then prior to the step of insertion of the cannulated instrument 106 it is possible to provide for the insertion of at least one milling tool 114, in a guided manner by way of the guiding element 103 through the percutaneous anterolateral access 2, in order to mill the bone structure 8 in order to create a passage through which the cannulated instrument 106 is then inserted.

Conveniently, the milling tool 114 is inserted, with its bit protected by an extractable sheath so that the bit, provided with a cutting edge, does not create lacerations during passage through the muscles but simply parts the fibers until it reaches the bone structure 8 to be operated on.

Once the operation has taken place, one proceeds with the extraction of the milling tool 114 through the percutaneous anterolateral access 2.

Conveniently, the steps of insertion and/or extraction of the milling tool 114, of the surgical instruments 106, 109, 111, 112 and 113, of the guiding wire 105 and of the intervertebral prosthesis 3 can be monitored at least partially by way of second radiographs taken with the aid of the radiological device mentioned earlier.

In addition, there can be a neurological device, not shown for the sake of graphical simplicity, with one pole that can be connected electrically to the surgical instruments and with the other pole that can be connected to the nervous system of the patient 101 so as to warn the surgeon if the surgical instrument being used is proximate to the nervous structures of the patient 101.

In summary, the surgical method described above can therefore avail of an apparatus that comprises:
an operating table 100, on which the patient 101 to be operated on is rested;
surgical instruments required for the surgical procedure;
a radiological device adapted to take radiographs in order to determine the exact position of the intervertebral disc 1 on which to operate and the optimal direction for guiding the surgical instruments;
a guiding wire 105, which can be inserted in the patient 101 through a percutaneous anterolateral access 2 along a direction that is substantially perpendicular and parallel, respectively, to the craniocaudal axis and to the sagittal axis of the patient 101, in such a manner that the surgical instruments are slideably associated with the guiding wire 105 in order to perform the surgical procedure in a wire-guided manner.

Advantageously, the guiding wire 105 can be of the type divided into centimeters, i.e., it can have a preset length so as to be able to limit the use of the radiological device to only the initial steps of the operation, since it is known where the guiding wire 105 is positioned in the intervertebral disc 1 by virtue of the first radiograph and if it is known how far the surgical instrument being used has translated with respect to said guiding wire 105, even without having visual confirmation there is always certainty as to where the surgical instrument being used is operating.

As regards the previously mentioned surgical instruments, these comprise:
at least one scalpel at the opening of the percutaneous anterolateral access 2;
at least one cannulated instrument 106, which is adapted to be inserted in the patient 101 through the percutaneous anterolateral access 2 along a direction that is substantially perpendicular and parallel, respectively, to the craniocaudal axis and to the sagittal axis of the patient 101.

Advantageously, as already noted, the cannulated instrument 106 is beveled at its distal tip so as to avoid damaging any nervous structures that may be present and is provided internally with a plug element 107 that is beveled at its distal tip so as to avoid damaging any nervous structures that may be present and is removable for the insertion of the guiding wire 105 once the cannulated instrument 106 has been positioned proximate to the intervertebral disc 1.

Furthermore, the surgical instruments comprise:
at least one hernia clamp 109, provided with an external cannulation 110 that is slideably associable with the guiding wire 105 in an eccentric manner with respect to the longitudinal axis of said hernia clamp 109 for the wire-guided insertion of the latter in the patient 101 and in order to remove the part of the intervertebral disc 1 that will be replaced by the intervertebral prosthesis 3, by rotating around the guiding wire 105;
at least one cannulated rasp 111, for example of the motorized type, which can be slideably associated with the guiding wire 105 for its wire-guided insertion in the patient 101 so as to be able to remove the cartilage of the vertebral endplates 5 and 6 that are adjacent to the intervertebral disc 1 and cause their bleeding so as to facilitate bone fusion between the intervertebral prosthesis 3 and said vertebral endplates 5 and 6;
at least one cannulated measurer 112, which can be slideably associated with the guiding wire 105 for its wire-guided insertion in the patient 101 so as to be able to determine the height of the intervertebral prosthesis 3 to be implanted.

Advantageously, as already noted, the cannulated measurer 112 has, at its distal part, substantially the shape of a parallelepiped with radiused edges and a substantially rectangular transverse cross-section, so as to be inserted in the intervertebral disc 1, where the intervertebral prosthesis 3 will be positioned, so that its lesser transverse thickness is substantially oriented along the craniocaudal axis of the patient 101.

In greater detail, the cannulated measurer 112 can rotate about the guiding wire 105 in such a manner as to be able to restore the intervertebral space between the intervertebral endplates 5 and 6, it being possible to position it so that its greater transverse thickness is substantially oriented along the craniocaudal axis of the patient 101 as a consequence of a 90° rotation of said cannulated measurer 112.

Furthermore, such surgical instruments comprise at least one insertion instrument 113, which can be associated at its distal part with the intervertebral prosthesis 3 to be implanted, is substantially shaped like a cannula and is slideably associable with the guiding wire 105 for its wire-guided insertion in the patient 101 so as to be able to correctly position the intervertebral prosthesis 3.

Advantageously, such insertion instrument 113 has, at its distal part, a threaded shank 115 that can engage a threaded hole 7, which is defined in the intervertebral prosthesis 3 at a side wall of the intervertebral prosthesis 3 substantially coaxially to a through-hole 9 that passes through the intervertebral prosthesis 3 from side to side along a direction parallel to the sagittal axis of the patient 101 and is adapted to slideably accommodate the guiding wire 105, so as to be able to transversely move the intervertebral prosthesis 3 within the intervertebral space and so that it can be unscrewed from the intervertebral prosthesis 3 so that it can be removed from the patient 101.

Conveniently, the threaded hole 7 has a larger diameter than the through-hole 9.

To complete the surgical instruments, these comprise:
- at least one milling tool 114, which can be inserted in the patient 101 through the percutaneous anterolateral access 2 and is adapted to create a through-hole through any bone structures, such as for example the iliac crest 8, that interfere with the operating trajectory 104;
- an articulated arm 102, for example of the motorized type, which can be fixed to the operating table 101 or to the spinous process of the patient 101 or to the bars of the arthrodesis, if they are present, and is provided, at its movable end, with a guiding element 103 that is adapted to support and guide the surgical instruments described so far and to support the guiding wire 105 during the surgical procedure;
- a neurological device with one pole that can be connected electrically to the surgical instruments and with the other pole that can be connected to the nervous system of the patient 101 in such a manner as to warn the surgeon if the surgical instrument being used is proximate to the nervous structures of the patient 101.

In greater detail, as already mentioned, the guiding element 103 can be positioned by way of the articulated arm 102, with respect to the intervertebral disc 1 to be operated on, at least along three degrees of freedom that are substantially parallel, respectively, to the craniocaudal axis, to the sagittal axis and to the latero-lateral axis of the patient 101.

Figure 24:
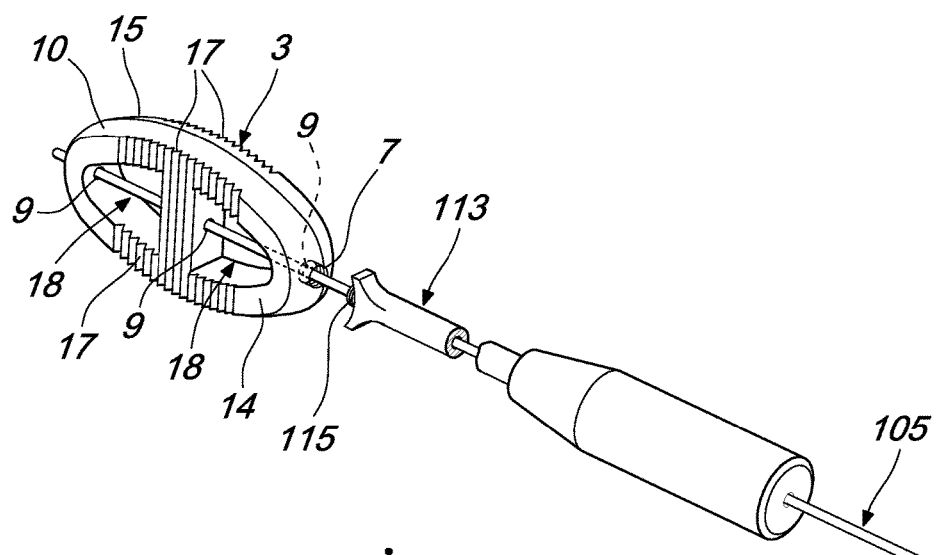
FIG. 24 is an exploded perspective view of the intervertebral prosthesis and of part of the inserted instrument, according to the present invention.
Figure 25:
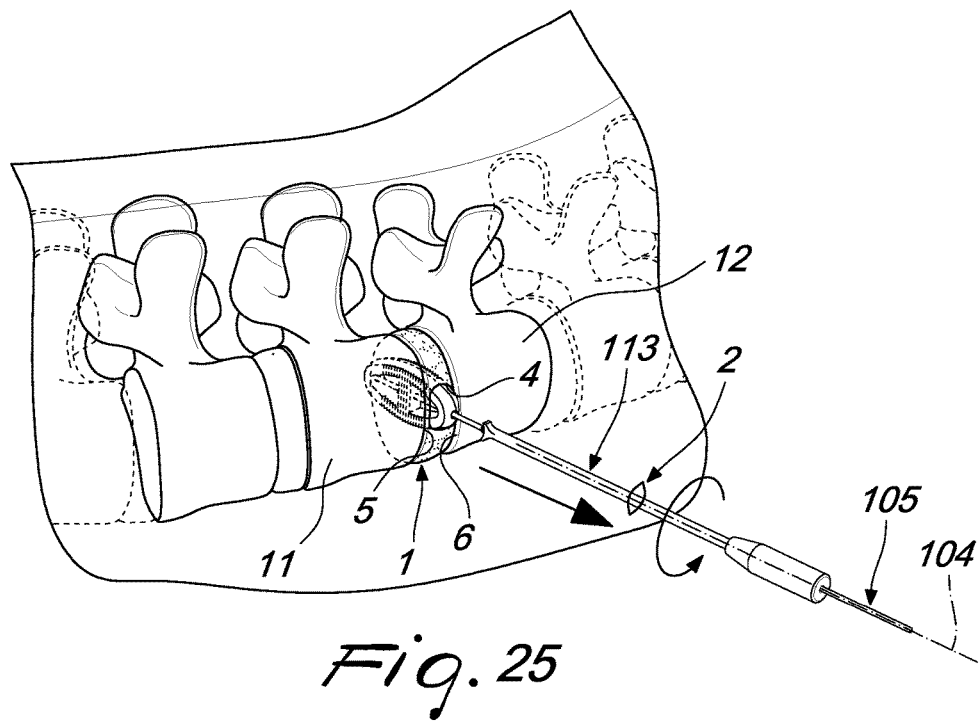
FIGS. 25 to 26 are two views, respectively a perspective view and a plan view from above, of a representation of the step of extraction of the cannulated instrument once the intervertebral prosthesis has been positioned, according to the present invention.
Figure 26:
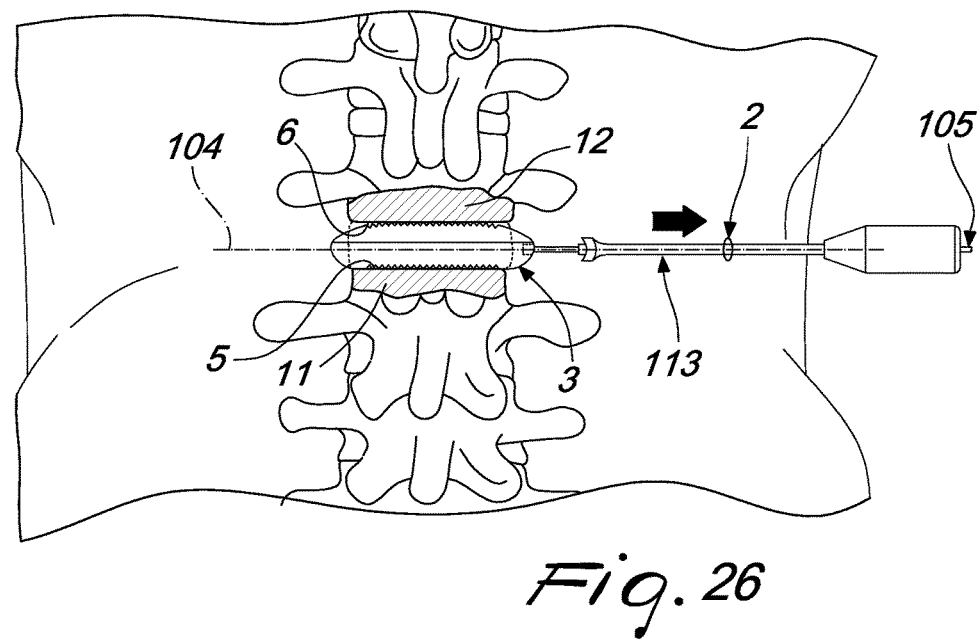
Figure 27:
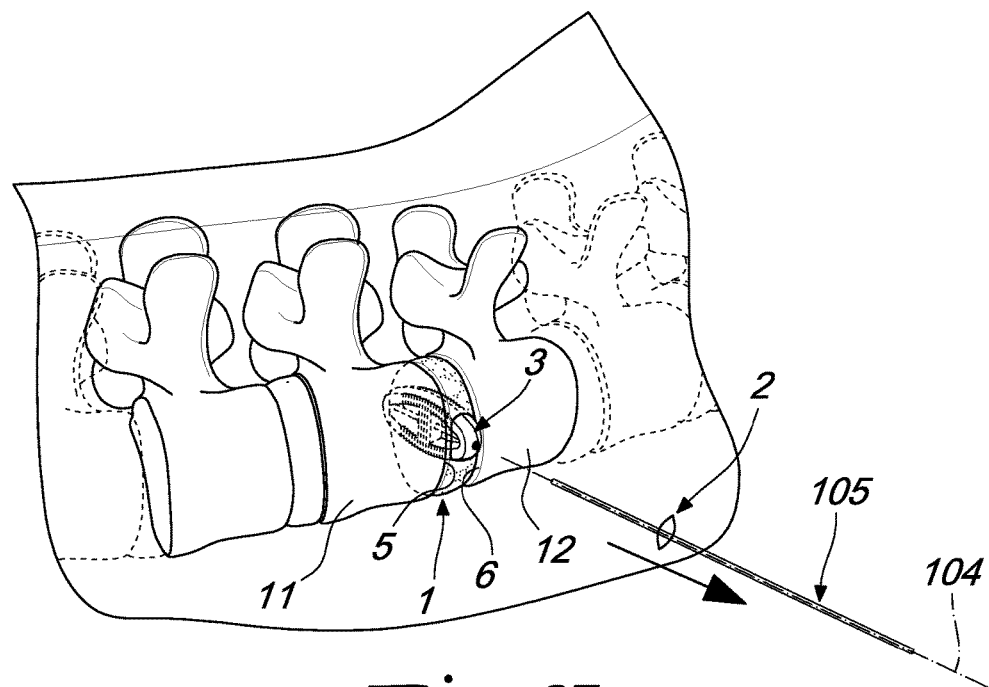
FIGS. 27 to 28 are two views, respectively a perspective view and a plan view from above, of a representation of the step of extraction of the guiding wire once the intervertebral prosthesis has been positioned, according to the present invention.
Figure 28:
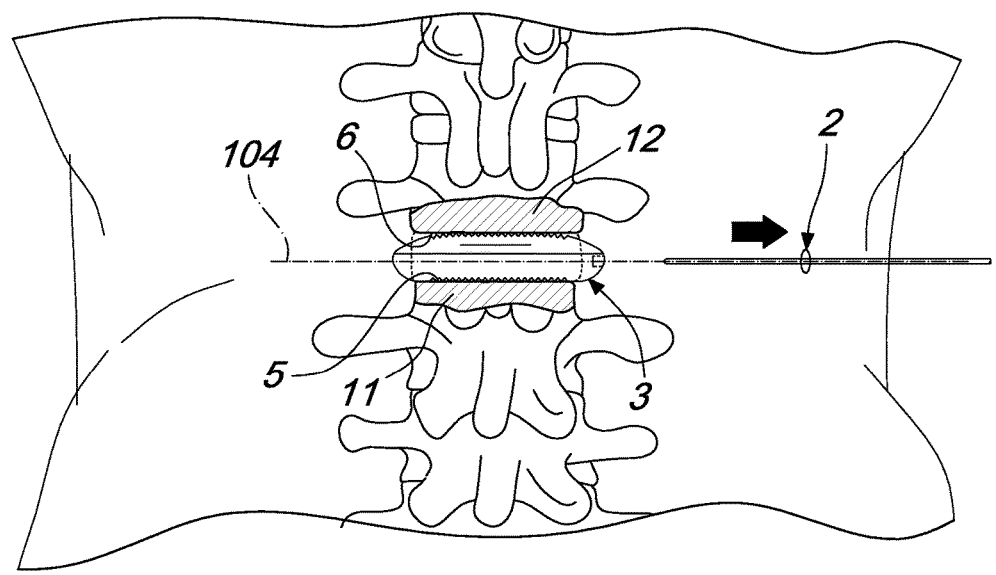

As regards the intervertebral prosthesis 3, which can be made of osteoconductive material so as to facilitate fusion with the adjacent vertebrae 11 and 12 between which it is inserted, as shown in FIG. 24, said prosthesis comprises an element 10 that has a substantially disc-like shape and is adapted to be inserted between two adjacent vertebrae 11 and 12 of the patient 101 in place of the intervertebral disc 1 comprised between them, so as to entirely support the vertebral endplates over the largest possible surface and, simultaneously, impart an anteroposterior angle that is aimed at maintaining physiological lordosis and sagittal balance in order to form a bone bridge between the adjacent vertebrae 11 and 12.

As already introduced previously, the element 10 has a through-hole 9 that passes through it from side to side and is adapted to slideably accommodate the guiding wire 105, previously inserted in the patient 101 along a direction that is parallel to the sagittal axis of the patient 101 through a percutaneous anterolateral access 2, for the wire-guided insertion of the intervertebral prosthesis 3.

Conveniently, the through-hole 9 extends along a radial direction with respect to the geometry of the element 10 so that it is oriented, once implanted, along a direction that is substantially perpendicular and parallel, respectively, to the craniocaudal axis and to the sagittal axis of the patient 101.

In this manner, the threaded hole 7, which is defined at a side wall of the element 10, is substantially coaxial to the through-hole 9, with a larger diameter than the through-hole 9.

Furthermore, the element 10 has, at its upper face 14 and at its lower face 15, which are intended to come into contact with the vertebral endplates 5 and 6 of the adjacent vertebrae DD and 12, a surface that is provided with a plurality of protruding bodies 17, which consist for example of toothed ridges and are adapted to facilitate the grip of the intervertebral prosthesis 3 with the vertebral endplates 5 and 6.

Finally, the element 10 has at least one lightening cavity 18 that passes through it from the upper face 14 to the lower face 15.

In practice it has been found that the intervertebral prosthesis, the apparatus for implanting intervertebral prostheses and the surgical method for implanting intervertebral prosthesis, particularly for percutaneous minimally-invasive surgical procedures, according to the invention, fully achieve the intended aim and objects, since they make it possible to achieve an intervertebral fusion adapted to create a bone bridge between two adjacent vertebrae with a percutaneous minimally-invasive surgical procedure.

In particular, by virtue of the fact that no retractor or distractor instruments are required and instead the intermediate structures (muscles) are passed through with the instruments and ultimately with the implant, it is possible to avoid problems related to stretching or compression of the femoral plexus.

The passage through the muscles in fact lasts only a few seconds for each instrument and the maximum size of the passage is the size of the cage, which in the maximum size is 15 by 22 millimeters. Furthermore, all the instruments and the implant itself are tapered in order to avoid tearing the structures through which they pass.

Another advantage of the intervertebral prosthesis, of the apparatus and of the surgical method according to the present invention consists in that, by virtue of the fact that the patient is placed in a prone position, the aorta and vena cava vascular structures and the abdominal organs in a prone position, presumably by gravity, move away from the operating corridor of the lateral access pathway.

A further advantage of the intervertebral prosthesis, of the apparatus and of the surgical method according to the present invention consists in that the annulus is not removed but only a small initial opening is created; since the structure of the annulus is furthermore made of X-crossed fibers, successive passages tend to open them without tearing them; this allows, once the implant has been inserted, the fibers of the annulus that have been passed through to close on themselves, in turn containing the implant and avoiding its dislocation.

Another advantage of the intervertebral prosthesis, of the apparatus and of the surgical method according to the present invention consists in that with the prone position of the patient (with respect to the position on one side of the background art) it is possible, by way of maneuvers with the table of the patient, to restore the correct sagittal balance intraoperatively.

Another advantage of the intervertebral prosthesis, of the apparatus and of the surgical method according to the present invention consists in that it is possible to position the implant at the L5-S 1 level, currently being the only implant of this type that can be implanted at this level.

A further advantage of the intervertebral prosthesis, of the apparatus and of the surgical method according to the present invention consists in that the execution times of the procedure are considerably shorter than the background art, and for posterior arthrodesis are reduced by approximately 50%.

The intervertebral prosthesis, the apparatus for implanting intervertebral prostheses and the surgical method for implanting intervertebral prostheses, particularly for percutaneous minimally-invasive surgical procedures, thus conceived, are susceptible of numerous modifications and variations, all of which are within the scope of the accompanying claims.

Furthermore, all the details may be replaced with other, technically equivalent elements.

In practice, the materials used, as well as the contingent shapes and dimensions, may be any according to the requirements and to the state of the art.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An apparatus for implanting intervertebral prostheses, particularly for percutaneous minimally-invasive surgical procedures, comprising:
   an operating table on which the patient to be operated on is rested,
   surgical instruments required for the surgical procedure,
   a radiological device adapted to take radiographs in order to determine the exact position of the intervertebral disc on which to operate and the optimal direction for guiding the surgical instruments,
   wherein the apparatus comprises at least one guiding wire that can be inserted in the patient through a percutaneous anterolateral access along a direction that is substantially perpendicular and parallel, respectively, to the craniocaudal axis and to the sagittal axis of the patient, the surgical instruments being slideably associable with the guiding wire in order to perform the surgical procedure in a wire-guided manner,
   wherein the guiding wire is of the type divided into centimeters,
   wherein the surgical instruments comprise:
      at least one scalpel at the opening of the percutaneous anterolateral access;
      at least one cannulated instrument that is adapted to be inserted in the patient through the percutaneous anterolateral access along a direction that is substantially perpendicular and parallel, respectively, to the craniocaudal axis and to the sagittal axis, the cannulated instrument being beveled at its distal tip so as to avoid damaging any nervous structures that may be present and being provided internally with a plug element that is beveled at its distal tip so as to avoid damaging any nervous structures that may be present and is removable for the insertion of the guiding wire once the cannulated instrument has been positioned proximate to the intervertebral disc; and
      at least one hernia clamp which is provided with an external cannulation that can be slideably associated with the guiding wire in an eccentric manner with respect to the longitudinal axis of the at least one hernia clamp for the wire-guided insertion of the at least one hernia clamp in the patient and in order to remove the part of the intervertebral disc that will be replaced by an intervertebral prosthesis, by rotating about the guiding wire.

2. The apparatus according to claim 1, wherein the surgical instruments comprise at least one cannulated rasp that can be slideably associated with the guiding wire for its wire-guided insertion in the patient so as to be able to remove the cartilage of the vertebral endplates that are adjacent to the intervertebral disc and cause their bleeding, so as to facilitate bone fusion between the intervertebral prosthesis and the vertebral endplates.

3. The apparatus according to claim 2, wherein the at least one cannulated rasp is of the motorized type.

4. The apparatus according to claim 3, wherein the surgical instruments comprise at least one cannulated measurer that can be slideably associated with the guiding wire for its wire-guided insertion in the patient so as to be able to determine the height of the intervertebral prosthesis to be implanted.

5. The apparatus according to claim 4, wherein the cannulated measurer has, at its distal part, substantially the shape of a parallelepiped with rounded edges and a substantially rectangular transverse cross-section, so as to be inserted in the intervertebral disc, where the intervertebral prosthesis will be positioned, so that its lesser transverse thickness is substantially oriented along the craniocaudal axis, the cannulated measurer being able to rotate around the guiding wire so as to be able to restore the intervertebral space between the intervertebral endplates by positioning the cannulated measurer with its greater transverse thickness oriented substantially along the craniocaudal axis following a 90° rotation of the cannulated measurer.

6. The apparatus according to claim 5, wherein the surgical instruments comprise at least one insertion instrument that can be associated at its distal part with the intervertebral prosthesis to be implanted, is shaped substantially like a cannula and can be slideably associated with the guiding wire for its wire-guided insertion in the patient so as to be able to correctly position the intervertebral prosthesis, the at least one insertion instrument being disengageable from the intervertebral prosthesis in such a manner that it can be removed once the intervertebral prosthesis has been placed in the intervertebral space.

7. The apparatus according to claim 6, wherein the at least one insertion instrument has, at the distal part thereof, a threaded shank that can engage in a threaded hole, which is defined in the intervertebral prosthesis at a side wall of the intervertebral prosthesis substantially coaxially to a through-hole that passes through the intervertebral prosthesis from side to side along a direction parallel to the sagittal axis and is adapted to slideably accommodate the guiding wire, so as to be able to transversely move the intervertebral prosthesis within the intervertebral space and so that it can be unscrewed from the intervertebral prosthesis so that it can be removed from the patient, the threaded hole having a larger diameter than the through-hole.

8. The apparatus according to claim 7, wherein the surgical instruments comprise at least one milling tool that can be inserted in the patient through the percutaneous anterolateral access and is adapted to create a hole that passes through any bone structures that interfere with the operating trajectory.

9. The apparatus according to claim 8, further comprising an articulated arm which can be fixed to the operating table or to the spinous process of the patient or to the bars of the arthrodesis, if they are present, the articulated arm being provided, at its movable end, with a guiding element that is adapted to support and guide the surgical instruments and to support the guiding wire during the surgical procedure, the guiding element being arrangeable, by way of the articulated arm with respect to the intervertebral disc to be operated on, at least along three degrees of freedom that are substantially parallel, respectively, to the craniocaudal axis, to the sagittal axis and to the latero-lateral axis of the patient.

10. The apparatus according to claim 9, wherein the articulated arm is of the motorized type.

11. The apparatus according to claim 10, further comprising a neurological device with one pole that can be connected electrically to the surgical instruments and with the other pole that can be connected to the nervous system of the patient so as to warn the surgeon if the surgical instrument being used is proximate to the nervous structures of the patient.

12. The apparatus according to claim 9, further comprising a neurological device with one pole that can be connected electrically to the surgical instruments and with the other pole that can be connected to the nervous system of the patient so as to warn the surgeon if the surgical instrument being used is proximate to the nervous structures of the patient.

13. The apparatus according to claim 6, wherein the surgical instruments comprise at least one milling tool that can be inserted in the patient through the percutaneous anterolateral access and is adapted to create a through-hole through any bone structures that interfere with the operating trajectory.

14. The apparatus according to claim 13, further comprising an articulated arm which can be fixed to the operating table or to the spinous process of the patient or to the bars of the arthrodesis, if they are present, the articulated arm being provided, at its movable end, with a guiding element that is adapted to support and guide the surgical instruments and to support the guiding wire during the surgical procedure, the guiding element being arrangeable by way of the articulated arm with respect to the intervertebral disc to be operated on at least along three degrees of freedom that are substantially parallel, respectively, to the craniocaudal axis, to the sagittal axis and to the latero-lateral axis of the patient.

15. The apparatus according to claim 14, wherein the articulated arm is of the motorized type.

16. The apparatus according to claim 15, further comprising a neurological device with one pole that can be connected electrically to the surgical instruments and with the other pole that can be connected to the nervous system of the patient in such a manner as to warn the surgeon if the surgical instrument being used is proximate to the nervous structures of the patient.

17. The apparatus according to claim 14, further comprising a neurological device with one pole that can be connected electrically to the surgical instruments and with the other pole that can be connected to the nervous system of the patient so as to warn the surgeon if the surgical instrument being used is proximate to the nervous structures of the patient.

18. The apparatus according to claim 4, wherein the surgical instruments comprise at least one insertion instrument that can be associated at its distal part with the intervertebral prosthesis to be implanted, is shaped substantially like a cannula and can be slideably associated with the guiding wire for its wire-guided insertion in the patient so as to be able to correctly position the intervertebral prosthesis, the at least one insertion instrument being disengageable from the intervertebral prosthesis so that it can be removed once the intervertebral prosthesis has been placed in the intervertebral space.

19. The apparatus according to claim 18, wherein the at least one insertion instrument has, at the distal part thereof, a threaded shank that can engage a threaded hole, which is defined in the intervertebral prosthesis at a side wall of the intervertebral prosthesis substantially coaxially to a through-hole that passes through the intervertebral prosthesis from side to side along a direction parallel to the sagittal axis and is adapted to slideably accommodate the guiding wire, so to be able to transversely move the intervertebral prosthesis within the intervertebral space and so that it can be unscrewed from the intervertebral prosthesis so that it can be removed from the patient, the threaded hole having a larger diameter than the through-hole.

20. The apparatus according to claim 19, wherein the surgical instruments comprise at least one milling tool that can be inserted in the patient through the percutaneous anterolateral access and is adapted to create a hole that passes through any bone structures that interfere with the operating trajectory.

21. The apparatus according to claim 20, further comprising an articulated arm that can be fixed to the operating table or to the spinous process of the patient or to the bars of the arthrodesis, if they are present, the articulated arm being provided, at its movable end, with a guiding element that is adapted to support and guide the surgical instruments and to support the guiding wire during the surgical procedure, the guiding element being arrangeable by way of the articulated arm with respect to the intervertebral disc to be operated on at least along three degrees of freedom that are substantially parallel, respectively, to the craniocaudal axis, to the sagittal axis and to the latero-lateral axis of the patient.

22. The apparatus according to claim 21, wherein the articulated arm is of the motorized type.

23. The apparatus according to claim 22, further comprising a neurological device with one pole that can be connected electrically to the surgical instruments and with the other pole that can be connected to the nervous system of the patient so as to warn the surgeon if the surgical instrument being used is proximate to the nervous structures of the patient.

24. The apparatus according to claim 21, further comprising a neurological device with one pole that can be connected electrically to the surgical instruments and with the other pole that can be connected to the nervous system of the patient so as to warn the surgeon if the surgical instrument being used is proximate to the nervous structures of the patient.

25. The apparatus according to claim 18, wherein the surgical instruments comprise at least one milling tool that can be inserted in the patient through the percutaneous anterolateral access and is adapted to create a through-hole through any bone structures that interfere with the operating trajectory.

26. The apparatus according to claim 25, further comprising an articulated arm that can be fixed to the operating table or to the spinous process of the patient or to the bars of the arthrodesis, if they are present, the articulated arm being provided, at its movable end, with a guiding element that is adapted to support and guide the surgical instruments and to support the guiding wire during the surgical procedure, the guiding element being arrangeable, by way of the articulated arm, with respect to the intervertebral disc to be operated on at least along three degrees of freedom that are substantially parallel, respectively, to the craniocaudal axis, to the sagittal axis and to the latero-lateral axis of the patient.

27. The apparatus according to claim 26, wherein the articulated arm is of the motorized type.

28. The apparatus according to claim 27, further comprising a neurological device with one pole that can be connected electrically to the surgical instruments and with the other pole that can be connected to the nervous system of the patient so as to warn the surgeon if the surgical instrument being used is proximate to the nervous structures of the patient.

29. The apparatus according to claim 26, further comprising a neurological device with one pole that can be connected electrically to the surgical instruments and with the other pole that can be connected to the nervous system of the patient so as to warn the surgeon if the surgical instrument being used is proximate to the nervous structures of the patient.

30. A surgical method for implanting intervertebral prostheses, particularly for percutaneous minimally-invasive surgical procedures, comprising:
   placing a patient to be operated on, on an operating table,
   taking a first radiograph by way of a radiological device in order to establish the exact position of the intervertebral disc to be operated on,
   opening a percutaneous anterolateral access by way of a scalpel,
   inserting in the patient, through the percutaneous anterolateral access, a series of surgical instruments that are adapted to prepare the intervertebral disc to accommodate an intervertebral prosthesis,
   inserting the intervertebral prosthesis in the patient through the percutaneous anterolateral access,
   wherein the insertion steps are performed with the aid of a guiding wire, inserted previously in the patient through the percutaneous anterolateral access along a direction that is substantially perpendicular and parallel, respectively, to the craniocaudal axis and to the sagittal axis of the patient, the surgical instruments and the intervertebral prosthesis being slideably associable with the guiding wire in order to perform the surgical procedure in a wire-guided manner,
   wherein, prior to the insertion steps, an articulated arm is fixed to the operating table or to the spinous process of the patient or to the bars of the arthrodesis, if they are present, in such a manner as to position a guiding element, with which the articulated arm is provided, which is adapted to support and guide the surgical instruments and to support the guiding wire during the surgical procedure, the guiding element defining an operating trajectory that is oriented along a direction that is substantially perpendicular and parallel, respectively, to the craniocaudal axis and to the sagittal axis,
   wherein, prior to the step of the insertion the series of surgical instruments and if there are bone structures present that interfere with the operating trajectory imposed by the guiding element in the direction of the intervertebral disc, the following are performed:
      the insertion of at least one milling tool, in a guided manner by way of the guiding element through the percutaneous anterolateral axis,
      the milling of the bone structure to create a passage through which the cannulated instrument is to be inserted,
      the extraction of the at least one milling tool through the percutaneous anterolateral access,
   wherein the step of insertion of the series of surgical instruments comprises:
      the insertion of at least one cannulated instrument, provided internally with a removable plug element, until the intervertebral disc is reached, the at least one cannulated instrument and the plug element being beveled at their distal tips so as to avoid damaging any nervous structures that may be present, the at least one cannulated instrument being inserted with the aid of the guiding element along the operating trajectory,
      the removal of the plug element,
      the insertion of the guiding wire in the cannulated instrument and the penetration of the intervertebral disc by the guiding wire for a depth that is less than the transverse thickness of the intervertebral disc,
      the extraction of the cannulated instrument through the percutaneous anterolateral access, slipping it off the guiding wire, which remains stationary,
      the wire-guided insertion of at least one hernia clamp provided with an external cannulation that can be slideably associated with the guiding wire in an eccentric manner with respect to the longitudinal axis of the at least one hernia clamp,
      the removal of part of the intervertebral disc with the aid of the at least one hernia clamp with rotation of the at least one hernia clamp around the guiding wire in order to create a seat for accommodating the intervertebral prosthesis that is delimited by the vertebral endplates that are adjacent to the intervertebral disc,
      the extraction of the at least one hernia clamp through the percutaneous anterolateral access, slipping it off the guiding wire, which remains stationary.

31. The surgical method according to claim 30, wherein the step of insertion of the series of surgical instrument comprises:
   the wire-guided insertion of at least one cannulated rasp,
   the removal, with the aid of the at least one cannulated rasp, of the cartilage of the vertebral endplates with bleeding thereof in such a manner as to facilitate bone fusion between the intervertebral prosthesis and the vertebral endplates,
   the extraction of the at least one cannulated rasp through the percutaneous anterolateral access, slipping it off the guiding wire, which remains stationary.

32. The surgical method according to claim 31, wherein the step of insertion of the series of surgical instruments comprises:
   the wire-guided insertion, where the intervertebral prosthesis will be positioned, and wire-guided extraction of a series of cannulated measurers of different sizes, having a shape, at their distal part, that is substantially parallelepiped with radiused edges and a substantially rectangular transverse cross-section, in succession with respect to each other so as to be able to determine the height of the intervertebral prosthesis to be implanted, the cannulated measurers being inserted in the intervertebral disc, so that their lesser transverse thickness is oriented substantially along the craniocaudal axis, if a compression of the intervertebral disc has occurred, the rotation through 90° of one of the cannulated measurers in such a manner as to position it with its greater transverse thickness oriented substantially along the craniocaudal axis, for the mutual spacing apart of the vertebral endplates, with consequent restoring of the intervertebral space between the intervertebral endplates, the extraction of the cannulated measurer through the percutaneous anterolateral access, slipping it off the guiding wire, which remains stationary.

33. The surgical method according to claim 32, wherein the step of insertion of the intervertebral prosthesis comprises:

the wire-guided insertion of at least one insertion instrument that supports, at its distal part, the intervertebral prosthesis so as to correctly position the intervertebral prosthesis in the previously prepared intervertebral space, the intervertebral prosthesis being wire-guided and being associated detachably with the at least one insertion instrument by shape mating, the disengagement of the at least one insertion instrument from the intervertebral prosthesis, with the intervertebral prosthesis arranged in the intervertebral space, for the extraction of the at least one insertion instrument and of the guiding wire.

34. The surgical method according to claim 33, wherein the steps of insertion and/or extraction of the milling tool, of the series of surgical instruments and of the intervertebral prosthesis are at least partly monitored by way of second radiographs taken with the aid of the radiological device.

35. The surgical method according to claim 34, wherein in the steps of insertion and/or extraction of the milling tool, of the series of surgical instruments and of the intervertebral prosthesis at least the milling tool and the at least one cannulated instrument are connected electrically to a pole of a neurological device, the other pole of the neurological device being connected electrically to the nervous system of the patient so as to warn the surgeon if the surgical instrument being used is proximate to the nervous structures of the patient.

* * * * *